(12) United States Patent
Reo et al.

(10) Patent No.: US 11,129,972 B2
(45) Date of Patent: Sep. 28, 2021

(54) PARANASAL SINUS FLUID ACCESS IMPLANTATION TOOLS, ASSEMBLIES, KITS AND METHODS

(71) Applicant: Sinopsys Surgical, Inc., Boulder, CO (US)

(72) Inventors: Michael Lawrence Reo, Redwood City, CA (US); Stephen Nicholas Bower, Morgan Hill, CA (US); Gary B. Hulme, San Jose, CA (US); Ronan L. Jenkinson, Gilbert, AZ (US); Justin Aaron Lance, Hollister, CA (US)

(73) Assignee: SINOPSYS SURGICAL, INC., Boulder, CO (US)

( * ) Notice: Subject to any disclaimer, the term of this patent is extended or adjusted under 35 U.S.C. 154(b) by 200 days.

(21) Appl. No.: 16/326,753

(22) PCT Filed: Sep. 20, 2018

(86) PCT No.: PCT/US2018/052038
§ 371 (c)(1),
(2) Date: Feb. 20, 2019

(87) PCT Pub. No.: WO2019/060605
PCT Pub. Date: Mar. 28, 2019

(65) Prior Publication Data
US 2021/0008356 A1 Jan. 14, 2021

Related U.S. Application Data

(60) Provisional application No. 62/561,095, filed on Sep. 20, 2017.

(51) Int. Cl.
*A61M 27/00* (2006.01)
*A61B 17/34* (2006.01)
*A61B 17/00* (2006.01)

(52) U.S. Cl.
CPC ....... *A61M 27/002* (2013.01); *A61B 17/3468* (2013.01); *A61B 2017/00367* (2013.01);
(Continued)

(58) Field of Classification Search
CPC ................ A61F 2/95; A61F 2002/9505; A61F 2002/9511; A61F 2002/9528; A61F 2002/9534; A61F 2002/9665
See application file for complete search history.

(56) References Cited

U.S. PATENT DOCUMENTS

| 3,726,284 A | 4/1973 | Parker |
| 3,948,272 A | 4/1976 | Guibor |

(Continued)

FOREIGN PATENT DOCUMENTS

| CN | 2077268 U | 5/1991 |
| FR | 2813522 A1 | 3/2002 |

(Continued)

OTHER PUBLICATIONS

Sadeghi et al.; "Transnasal Endoscopic Medial Maxillectomy for Inverting Papilloma"; Laryngoscope; Apr. 1, 2003 113:749-753.

(Continued)

*Primary Examiner* — Adam Marcetich
(74) *Attorney, Agent, or Firm* — Dorsey & Whitney LLP

(57) ABSTRACT

An implantation tool to implant a paranasal sinus fluid access implant device to fluidly connect the lacrimal apparatus in the orbit with a paranasal sinus has a securement mechanism reconfigurable from a securement configuration to secure the implant device to a mounting portion of a carrier member to a released configuration to release the implant device from the carrier member, and with a release mechanism disposed at least partially in an interior working space housed within the implantation tool. An implantation method with an approach through the palpebral fissure (Continued)

advances the implant device through a surgical route mostly under tension.

33 Claims, 18 Drawing Sheets

(52) U.S. Cl.
CPC .............. *A61B 2017/00477* (2013.01); *A61M 2210/0612* (2013.01); *A61M 2210/0681* (2013.01)

(56) References Cited

U.S. PATENT DOCUMENTS

| | | | |
|---|---|---|---|
| 4,915,684 A | 4/1990 | MacKeen et al. | |
| 4,921,485 A | 5/1990 | Griffiths | |
| 5,169,386 A | 12/1992 | Becker et al. | |
| 5,318,513 A | 6/1994 | Leib et al. | |
| 5,345,948 A | 9/1994 | O'Donnell, Jr. | |
| 5,405,378 A * | 4/1995 | Strecker | A61F 2/04 |
| | | | 606/194 |
| 6,041,785 A | 3/2000 | Webb | |
| 6,083,188 A | 7/2000 | Becker | |
| 6,113,567 A | 9/2000 | Becker | |
| 6,629,533 B1 | 10/2003 | Webb et al. | |
| 6,878,165 B2 | 4/2005 | Makino | |
| 6,966,888 B2 | 11/2005 | Cullen et al. | |
| 7,156,821 B2 | 1/2007 | Dohlman | |
| 7,169,163 B2 | 1/2007 | Becker | |
| 7,361,168 B2 | 4/2008 | Makower et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 7,500,971 B2 | 3/2009 | Chang et al. | |
| D590,935 S | 4/2009 | Becker | |
| 7,547,323 B2 | 6/2009 | Lavigne | |
| 7,559,925 B2 | 7/2009 | Goldfarb et al. | |
| 7,641,644 B2 | 1/2010 | Chang et al. | |
| 7,645,272 B2 | 1/2010 | Chang et al. | |
| 7,654,997 B2 | 2/2010 | Makower et al. | |
| 7,713,255 B2 | 5/2010 | Eaton et al. | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,758,534 B2 | 7/2010 | Pearson | |
| 7,771,409 B2 | 8/2010 | Chang et al. | |
| 7,785,315 B1 | 8/2010 | Muni et al. | |
| 7,803,150 B2 | 9/2010 | Chang et al. | |
| 7,846,124 B2 | 12/2010 | Becker | |
| 9,022,967 B2 | 5/2015 | Oliver et al. | |
| 9,308,358 B2 | 4/2016 | Oliver et al. | |
| 9,561,350 B2 | 2/2017 | Willoughby et al. | |
| 9,572,964 B2 | 2/2017 | Ross et al. | |
| 9,700,459 B2 | 7/2017 | Willoughby et al. | |
| 9,901,721 B2 | 2/2018 | Oliver et al. | |
| 10,035,004 B2 | 7/2018 | Oliver et al. | |
| 2002/0032444 A1 | 3/2002 | Mische | |
| 2002/0107579 A1 | 8/2002 | Makino | |
| 2004/0064150 A1 | 4/2004 | Becker | |
| 2004/0077989 A1 | 4/2004 | Goode et al. | |
| 2004/0116958 A1 | 6/2004 | Gopferich et al. | |
| 2004/0148008 A1 * | 7/2004 | Goodson, IV | A61F 2/962 |
| | | | 623/1.12 |
| 2004/0204704 A1 | 10/2004 | Tamplenizza et al. | |
| 2004/0254516 A1 | 12/2004 | Murray et al. | |
| 2005/0085891 A1 * | 4/2005 | Goto | A61F 2/94 |
| | | | 623/1.11 |
| 2005/0197614 A1 | 9/2005 | Pritchard et al. | |
| 2005/0240143 A1 | 10/2005 | Dohlman | |
| 2005/0245906 A1 | 11/2005 | Makower et al. | |
| 2005/0273033 A1 | 12/2005 | Grahn et al. | |
| 2006/0063973 A1 | 3/2006 | Makower et al. | |
| 2006/0142736 A1 | 6/2006 | Hissink et al. | |
| 2006/0251575 A1 | 11/2006 | Morgenstern | |
| 2006/0276738 A1 | 12/2006 | Becker | |
| 2006/0276873 A1 * | 12/2006 | Sato | A61F 2/94 |
| | | | 623/1.11 |
| 2007/0005120 A1 | 1/2007 | Villacampa et al. | |
| 2007/0112291 A1 | 5/2007 | Borgensen | |
| 2007/0129751 A1 | 6/2007 | Muni et al. | |
| 2007/0135789 A1 | 6/2007 | Chang et al. | |
| 2007/0167682 A1 | 7/2007 | Goldfarb et al. | |
| 2007/0208252 A1 | 9/2007 | Makower | |
| 2007/0208301 A1 | 9/2007 | Evard et al. | |
| 2007/0249896 A1 | 10/2007 | Goldfarb et al. | |
| 2007/0255263 A1 | 11/2007 | Sugimoto | |
| 2007/0269487 A1 | 11/2007 | de Juan et al. | |
| 2007/0276314 A1 | 11/2007 | Becker | |
| 2007/0282305 A1 | 12/2007 | Goldfarb et al. | |
| 2007/0293726 A1 | 12/2007 | Goldfarb et al. | |
| 2007/0293727 A1 | 12/2007 | Goldfarb et al. | |
| 2007/0293929 A1 * | 12/2007 | Aoba | A61F 2/95 |
| | | | 623/1.11 |
| 2008/0082037 A1 | 4/2008 | Pearson | |
| 2008/0097154 A1 | 4/2008 | Makower et al. | |
| 2008/0097354 A1 | 4/2008 | Lavigne | |
| 2008/0097514 A1 | 4/2008 | Chang et al. | |
| 2008/0103361 A1 | 5/2008 | Makower et al. | |
| 2008/0103521 A1 | 5/2008 | Makower et al. | |
| 2008/0119693 A1 | 5/2008 | Makower et al. | |
| 2008/0125626 A1 | 5/2008 | Chang et al. | |
| 2008/0125805 A1 | 5/2008 | Mische | |
| 2008/0132938 A1 | 6/2008 | Chang et al. | |
| 2008/0154237 A1 | 6/2008 | Chang et al. | |
| 2008/0154250 A1 | 6/2008 | Makower et al. | |
| 2008/0195041 A1 | 8/2008 | Goldfarb et al. | |
| 2008/0228085 A1 | 9/2008 | Jenkins et al. | |
| 2008/0234720 A1 | 9/2008 | Chang et al. | |
| 2008/0275483 A1 | 11/2008 | Makower et al. | |
| 2008/0281156 A1 | 11/2008 | Makower et al. | |
| 2008/0287908 A1 | 11/2008 | Muni et al. | |
| 2008/0288045 A1 * | 11/2008 | Saeed | A61F 2/07 |
| | | | 623/1.14 |
| 2008/0306428 A1 | 12/2008 | Becker | |
| 2008/0319424 A1 | 12/2008 | Muni et al. | |
| 2009/0005763 A1 | 1/2009 | Makower et al. | |
| 2009/0028923 A1 | 1/2009 | Muni et al. | |
| 2009/0030274 A1 | 1/2009 | Goldfarb et al. | |
| 2009/0036818 A1 | 2/2009 | Grahn et al. | |
| 2009/0099626 A1 | 4/2009 | de Juan, Jr. et al. | |
| 2009/0104248 A1 | 4/2009 | Rapacki et al. | |
| 2009/0105749 A1 | 4/2009 | de Juan, Jr. et al. | |
| 2009/0187098 A1 | 7/2009 | Makower et al. | |
| 2009/0198216 A1 | 8/2009 | Muni et al. | |
| 2009/0204142 A1 | 8/2009 | Becker | |
| 2009/0221988 A1 | 9/2009 | Ressemann et al. | |
| 2009/0240112 A1 | 9/2009 | Goldfarb et al. | |
| 2009/0240237 A1 | 9/2009 | Goldfarb et al. | |
| 2009/0275882 A1 | 11/2009 | Lavigne | |
| 2009/0275903 A1 | 11/2009 | Lavigne | |
| 2009/0281621 A1 | 11/2009 | Becker | |
| 2009/0298390 A1 | 12/2009 | Rapacki et al. | |
| 2009/0312745 A1 | 12/2009 | Goldfarb et al. | |
| 2009/0312829 A1 * | 12/2009 | Aoba | A61F 2/95 |
| | | | 623/1.11 |
| 2010/0034870 A1 | 2/2010 | Sim et al. | |
| 2010/0042046 A1 | 2/2010 | Chang et al. | |
| 2010/0076269 A1 | 3/2010 | Makower et al. | |
| 2010/0099946 A1 | 4/2010 | Jenkins et al. | |
| 2010/0100181 A1 | 4/2010 | Makower et al. | |
| 2010/0106255 A1 | 4/2010 | Dubin | |
| 2010/0114066 A1 | 5/2010 | Makower et al. | |
| 2010/0121308 A1 | 5/2010 | Muni et al. | |
| 2010/0174138 A1 | 7/2010 | Chang et al. | |
| 2010/0174308 A1 | 7/2010 | Chang et al. | |
| 2010/0198247 A1 | 8/2010 | Chang et al. | |
| 2010/0210901 A1 | 8/2010 | Makower et al. | |
| 2010/0241054 A1 | 9/2010 | Dacey, Jr. et al. | |
| 2010/0268245 A1 | 10/2010 | Chang et al. | |
| 2010/0274204 A1 | 10/2010 | Rapacki et al. | |
| 2010/0274259 A1 | 10/2010 | Yaron et al. | |
| 2010/0298862 A1 | 11/2010 | Chang et al. | |
| 2010/0317969 A1 | 12/2010 | Becker | |

(56) References Cited

U.S. PATENT DOCUMENTS

| | | | |
|---|---|---|---|
| 2011/0004057 A1 | 1/2011 | Goldfarb et al. | |
| 2011/0056852 A1 | 3/2011 | Frojd | |
| 2011/0060214 A1 | 3/2011 | Makower | |
| 2011/0105989 A1 | 5/2011 | Becker | |
| 2011/0112512 A1 | 5/2011 | Muni et al. | |
| 2011/0224680 A1 | 9/2011 | Barker | |
| 2011/0276131 A1 | 11/2011 | de Juan, Jr. et al. | |
| 2011/0288624 A1* | 11/2011 | Roeder | A61F 2/95 623/1.11 |
| 2011/0311601 A1 | 12/2011 | Kleine et al. | |
| 2012/0041535 A1* | 2/2012 | Huser | A61F 2/966 623/1.11 |
| 2012/0089071 A1 | 4/2012 | Oliver et al. | |
| 2012/0245539 A1 | 9/2012 | Zarins et al. | |
| 2013/0030545 A1 | 1/2013 | Gross et al. | |
| 2013/0231693 A1 | 9/2013 | Edgren et al. | |
| 2013/0274647 A1 | 10/2013 | Oliver et al. | |
| 2014/0012309 A1 | 1/2014 | Keith et al. | |
| 2014/0120146 A1 | 5/2014 | Nakamura et al. | |
| 2014/0135478 A1 | 5/2014 | Chaix et al. | |
| 2014/0135916 A1 | 5/2014 | Clauson et al. | |
| 2014/0277350 A1* | 9/2014 | Melsheimer | A61F 2/07 623/1.11 |
| 2015/0065941 A1 | 3/2015 | Ross et al. | |
| 2015/0073525 A1* | 3/2015 | Aoba | A61F 2/966 623/1.11 |
| 2015/0157835 A1 | 6/2015 | Oliver et al. | |
| 2015/0231376 A1 | 8/2015 | Willoughby et al. | |
| 2016/0045347 A1* | 2/2016 | Smouse | A61F 2/95 623/23.66 |
| 2016/0120676 A1* | 5/2016 | Gomes Nogueira | A61F 2/966 623/1.11 |
| 2016/0135992 A1 | 5/2016 | Schaller et al. | |
| 2016/0250070 A1 | 9/2016 | Willoughby et al. | |
| 2016/0271378 A1 | 9/2016 | Oliver et al. | |
| 2017/0165108 A1 | 6/2017 | Bianchi et al. | |
| 2017/0189212 A1* | 7/2017 | Eller | A61F 2/954 |
| 2017/0209678 A1 | 7/2017 | Willoughby et al. | |
| 2017/0216094 A1 | 8/2017 | Reo et al. | |
| 2017/0290692 A1* | 10/2017 | Toner | A61F 2/97 |
| 2018/0126131 A1 | 5/2018 | Oliver et al. | |
| 2019/0015643 A1 | 1/2019 | Oliver et al. | |

FOREIGN PATENT DOCUMENTS

| | | |
|---|---|---|
| WO | 01078631 A2 | 10/2001 |
| WO | 2005000154 A2 | 1/2005 |
| WO | 2006133066 A2 | 12/2006 |
| WO | 2007115259 A2 | 10/2007 |
| WO | 2008036671 A1 | 3/2008 |
| WO | 2008045242 A2 | 4/2008 |
| WO | 2009032328 A1 | 3/2009 |
| WO | 2009035562 A2 | 3/2009 |
| WO | 2009145755 A1 | 12/2009 |
| WO | 2010078145 A1 | 7/2010 |
| WO | 2010096822 A2 | 8/2010 |
| WO | 2010107826 A2 | 9/2010 |
| WO | 2010111528 A2 | 9/2010 |
| WO | 2011066479 A1 | 6/2011 |
| WO | 2012048278 A2 | 4/2012 |
| WO | 2013130468 A1 | 9/2013 |
| WO | 2013154843 A1 | 10/2013 |
| WO | 20140116980 A1 | 7/2014 |
| WO | 2015069433 A1 | 5/2015 |
| WO | 2016014996 A1 | 1/2016 |
| WO | 2017132573 A1 | 8/2017 |

OTHER PUBLICATIONS

Mangan et al.; "Bilateral Nasolacrimal Duct Atresia in a Cria"; Veterinary Opthalmology; Nov. 1, 2008; 11, 1; pp. 49-54.

Giuliano et al.; "Dacryocystomaxillorhinostomy for Chronic Dacryosystitis in a Dog"; Veterinary Opthalmology; 2006; 9, 2, pp. 89-94.

Bagdonaite et al.; "Twelve-Year Experience of Lester Jones Tubes—Results and Comparison of 3 Different Tube Types"; Opthalmic Plastic Reconstructive Surgery; Jan. 1, 2015; vol. 31, No. 5.; pp. 352-356.

Wilson et al.; "Surgical Reconstruction of the Nasolacrimal System in the Horse"; Equine Veterinary Science; Nov. 1, 1991; vol. II, No. 4; pp. 232-234.

Steinmetz et al.; "Surgical Removal of a Dermoid Cyst from the Bony Part of the Nasolacrimal Duct in a Scottish Higland Cadle Heifer"; Veterinary Opthalmology; Dec. 1, 2009; 12, 4, pp. 259-262.

McIlnay et al.; "Use of Canaliculorhinostomy for Repair of Nasolacrimal Duct Obstruction in a Horse"; JAVMA; Jan. 1, 2001; vol. 218, No. 8; Scientific Reports: Clinical Report; pp. 1323-1324.

Gionfriddo Jr.; "The nasolacrimal system"; Textbook of Small Animal Surgery, 3rd Edition; Jan. 1, 2003; Slatter OM ed. Saunders, Philadelphia PA; pp. 1356-1358.

Tang et al.; "Influence of silicone surface roughness and hydrophobicity on adhesion and colonization of *Staphylococcus epidermidis*"; Journal of Biomedical Materials Research; Part A; 2008; vol. 88A, No. 2.; pp. 454-463.

\* cited by examiner

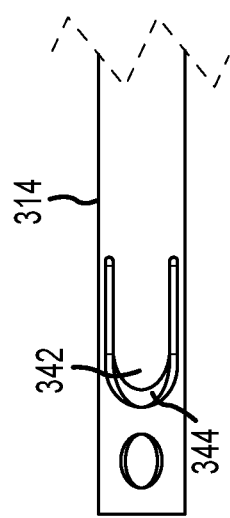
FIG.9
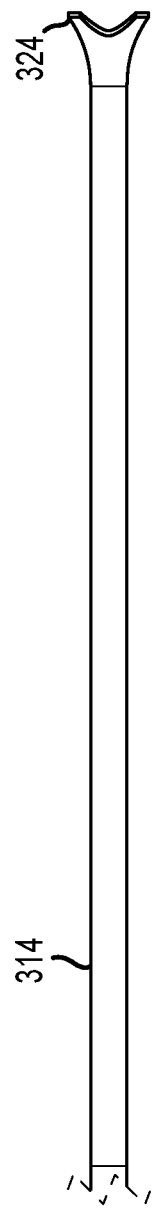
FIG.8
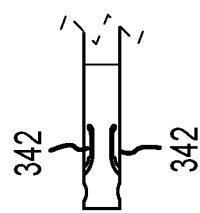

PARANASAL SINUS FLUID ACCESS IMPLANTATION TOOLS, ASSEMBLIES, KITS AND METHODS

CROSS-REFERENCE TO RELATED APPLICATIONS

This application claims the benefit of U.S. Provisional Application No. 62/561,095, entitled "PARANASAL SINUS FLUID ACCESS IMPLANTATION TOOLS, ASSEMBLIES, KITS AND METHODS" filed Sep. 20, 2017, the entire contents of which are incorporated herein by reference.

BACKGROUND

Millions of people are treated each year for infections of the paranasal sinuses, or sinusitis, with many of those suffering from chronic sinusitis. Conventional surgical interventions directed to providing enhanced irrigation and drainage may provide moderate symptomatic improvement but not a cure. Recent interventions have been proposed to directly access the paranasal sinuses to permit medical procedures or drug treatments to be performed more directly in the paranasal sinuses. Direct access to a paranasal sinus has been proposed from an approach through the nose and an ostium that provides a natural opening from the nasal cavity into a paranasal sinus. Such medical interventions to directly access a paranasal sinus through the natural opening of the ostium involve complex manipulations of access tools to and through the restricted space of the ostium.

Another more recent intervention is based on providing an artificial fluid communication path between the lacrimal apparatus and a paranasal sinus through a paranasal sinus access implant device implanted through an artificially formed surgical path between the lacrimal apparatus in the paranasal sinus to provide direct fluid communication access from the lacrimal apparatus to the paranasal sinus through an internal passage of the implanted implant device. One surgical approach is through the palpebral fissure to form a surgical path between the lacrimal apparatus in the orbit and a paranasal sinus, often the ethmoid sinus. Examples of some paranasal sinus access implant devices and implantation tools and procedures for implanting such implant devices to provide a fluid communication between the lacrimal apparatus and a paranasal sinus are disclosed for example in International Patent Application Publication Nos. WO 2012/048278 A2; WO 2013/154843 A1; WO 2014/116980 A1; WO 2015/069433 A1; WO 2016/014996 A1; WO 2016/015002 A1; and WO 2017/132573 A1 published by the World Intellectual Property Organization.

When implanted, such paranasal sinus access implant devices provide convenient access to the paranasal sinus for administration of drugs or irrigation fluid directly to the paranasal sinus or performance of medical procedures in the paranasal sinus. However, for enhanced compatibility and interaction with surgically-penetrated tissue, such paranasal sinus access implant devices may be made of relatively soft and flexible material, for example polymeric materials, such as medical grade silicone, having a Shore A hardness often in a range of about 60-80. Advancing such flexible implant devices through a properly sized surgical route, and without additional inflammation of tissue in and adjacent to the surgical path, can be difficult. Such implant devices may include anchor protrusions configured to interact with issue exposed in the surgical path to help anchor the implanted implant device. For enhanced fit through and retention in the surgical path, the outside diameter of the implant device may be larger than the diameter of the surgical cut made to form the surgical path, especially at locations of the anchor protrusions. Resistance to insertion through the surgical path when an implant device is advanced into and through the surgical path during an implantation procedure may result in accordion-like deformation of the flexible implant device that further increases resistance to advancement of the implant device and complicating performance of the implantation procedure and increasing potential for additional inflammation of tissue that can lead to patient discomfort and longer heal times. Additionally, the wall of the sinus bone that is penetrated by the surgical cut to access the paranasal sinus may be very thin and susceptible to fracture and breakage during the implantation procedure. Such fracturing and breakage of the wall of the sinus bone may be detrimental to good securement of the implanted device in the implantation position through the surgical cut, and is also not desired for good surgical practice.

Although surgical implantation techniques for implantation of such paranasal sinus access implant devices to fluidly connect the lacrimal apparatus in the orbit and a paranasal sinus have achieved a significant level of success in accessing and treating conditions of the paranasal sinuses, implantation tools and procedures still may suffer from one or more of these problems, and there is a significant need for improved implantation tools and procedures to further address such problems.

SUMMARY

The inventors have inventively recognized that these problems may be addressed at least in part for implantation of paranasal sinus access implant devices of the type summarized above implanted with a surgical approach through the palpebral fissure to provide an artificial fluid communication connection between the lacrimal apparatus in the orbit and a paranasal sinus by providing implantation tools and implantation procedures that maintain the paranasal access implant device mostly in tension as the implant device is advanced from the palpebral fissure approach through the surgical path during implantation procedure. Stated another way, when most of the length of the implant device that is advanced through the surgical path is pulled through the surgical path (in tension) rather than being pushed through the surgical path (in compression), the implant device is allowed to stretch out rather than bunch up in an accordion-like fashion during advancement into and through the surgical path, which eases advancement of the implant device through the surgical path and tends to reduce potential for causing fracture or breakage of the sinus wall bone, other tissue inflammation and the difficulty for the medical professional to perform the implantation procedure. A result may be both that the implantation procedure is faster and easier for a medical professional to perform and with reduced potential for surgical complications.

A first aspect of this disclosure provides an implantation tool to implant a paranasal sinus fluid access implant device with an internal fluid communication passage through an artificial, surgical path between a lacrimal apparatus in the orbit and a paranasal sinus in an implantation procedure to provide direct fluid communication access through the internal passage from the lacrimal apparatus in the orbit to the paranasal sinus. The implantation tool may include:
  a carrier member configured to carry the implant device on a mounting portion of the carrier member in a mounted orientation to position the implant device in an implantation position through the surgical path from an approach through the palpebral fissure during the implantation procedure;

a securement mechanism to secure the implant device in the implantation orientation on the carrier member to carry the implant device to the implantation position during the implantation procedure, the securement mechanism being reconfigurable from a securement configuration to secure the implant device to the mounting portion of the carrier member in the implantation orientation to a released configuration to release the implant device from securement to the carrier member to permit withdrawal of the carrier member relative to the implant device to leave the implant device implanted in the implantation position during the implantation procedure;

a handle portion connected with the carrier member and configured to remain outside of the surgical path during the implantation procedure and being manipulable by a medical practitioner to direct implantation of the implant device during the implantation procedure;

internal working space housed within at least a portion of the handle portion and at least a portion of the carrier member;

a release mechanism disposed at least in part in the internal working space and manipulable to reconfigure the securement mechanism from the securement configuration to the released configuration.

A second aspect of this disclosure provides an implantation assembly for implanting a paranasal sinus fluid access implant device through a surgical path between a lacrimal apparatus in the orbit and a paranasal sinus in an implantation procedure to provide direct fluid communication access from the lacrimal apparatus in the orbit to the paranasal sinus through an internal passage of the implant device. The implantation assembly of this second aspect may include:

such a paranasal sinus access implant device: and an implantation tool, wherein the implant device is mounted in a mounting orientation on a mounting portion of a carrier member of the implantation tool with a securement mechanism of the implantation tool in a securement configuration, and which securement mechanism is reconfigurable to a released configuration to release the implant device from securement to the mounting portion of the carrier member.

The implantation tool in the implantation assembly of this second aspect may be according to the first aspect of this disclosure.

A third aspect of this disclosure provides an implantation kit for implanting a paranasal sinus fluid access implant device through a surgical path between a lacrimal apparatus in the orbit and a paranasal sinus in an implantation procedure to provide direct fluid communication access from the lacrimal apparatus in the orbit to the paranasal sinus through an internal passage of the implant device. The implantation kit of this third aspect may include:

an implantation tool, wherein the implant device is mountable in a mounting orientation on a mounting portion of a carrier member of the implantation tool with a securement mechanism of the implantation tool in a securement configuration, and which securement mechanism is reconfigurable to a released configuration to release the implant device from securement to the mounting portion of the carrier member; and such a paranasal sinus access implant device;

wherein, the implantation tool and implant device are assembled or assemblable into an implantation assembly with the implant device mounted in the mounting orientation on the mounting portion of the carrier member with the securement mechanism in the securement configuration.

The implantation tool of the kit of this third aspect may be according to the first aspect of this disclosure. The implantation assembly of the kit of this third aspect may be according to the second aspect of this disclosure.

A fourth aspect of this disclosure provides a method for implanting a paranasal sinus access implant device to fluidly connect a lacrimal apparatus in the orbit with a paranasal sinus. The method of this fourth aspect may include:

with a surgical approach through the palpebral fissure, surgically forming an artificial surgical path between a location in a lacrimal apparatus in the orbit and a paranasal sinus;

advancing an implantation assembly including such a paranasal sinus access implant device from an approach through the palpebral fissure until the implant device extends through the surgical path in the implantation position, wherein the implantation assembly includes the implant device mounted in a mounting orientation on a mounting portion of a carrier member of an implantation tool with a securement mechanism of the implantation tool in a securement configuration, and which securement mechanism is reconfigurable to a released configuration to release the implant device from securement to the mounting portion of the carrier member;

manipulating the release mechanism to reconfigure the securement mechanism from the securement configuration to the released configuration;

withdrawing the implantation tool from the surgical path, leaving the implant device implanted through the surgical path fluidly connecting the lacrimal apparatus in the orbit with the paranasal sinus.

The implantation tool used in the method of this fourth aspect may be according to the first aspect of this disclosure. The implantation assembly used in the method of this fourth aspect may be according to the second aspect of this disclosure. The implant device and the implantation tool used in the implantation assembly used in the method of this fourth aspect may be provided in an implantation kit according to the third aspect of this disclosure.

A fifth aspect of this disclosure provides a method for implanting a paranasal sinus fluid access implant device through an artificial, surgical path between a lacrimal apparatus in the orbit and a paranasal sinus to provide direct fluid communication access from the lacrimal apparatus in the orbit to the paranasal sinus through an internal passage of the implant device. The method of this fifth aspect may include:

with the implant device secured to an exterior of a carrier member of an implantation tool with a distal end of the implant device disposed toward a distal end of the implantation tool and a proximal end of the implant device disposed toward a proximal end of the implantation tool and with an implantation approach from the lacrimal apparatus in the orbit, advancing the implant device through the surgical path between the lacrimal apparatus in an orbit and the paranasal sinus until the implant device is in an implantation position with the distal end of the implant device disposed in the paranasal sinus and the proximal end of the implant device disposed in the lacrimal apparatus in the orbit;

after the advancing, releasing the implant device from securement to the exterior of the carrier member and withdrawing the carrier member from the surgical path to leave the implant device implanted in the implantation position fluidly connecting the lacrimal apparatus in the orbit with the paranasal sinus through the internal passage of the implant device; and the implant device having a length from the proximal end to the distal end of the implant device;

wherein during the advancing a length portion of the implant device, which is smaller than the length of the implant device, enters into and advances at least some distance through the surgical path, and a majority of the length portion is in tension while advancing through the surgical path.

The method of this fifth aspect may include performance of the method of the fourth aspect of this disclosure. The implantation tool used in the method of this fifth aspect may be according to the first aspect. The implant device secured to an exterior of a carrier member of an implantation tool in the method of this fifth aspect may be provided in an implantation assembly according to the second aspect of this disclosure. The implant device and the implantation tool used in the method of this fifth aspect may be provided in an implantation kit according to the third aspect of this disclosure.

These and other aspects of this disclosure and features for use therewith are further described below. A number of feature refinements and additional features disclosed below are applicable to each of the aspects of this disclosure, including to an implantation tool, implantation assembly, implantation kit and an implantation method of any such aspect. These feature refinements and additional features may be used individually or in any combination in any or all of these aspects. As such, each of the features that will be discussed below may be, but are not required to be, used with any other feature or combination of features of the same or any other aspect of this disclosure.

Numerous additional features and advantages of the present disclosure will become apparent to those skilled in the art upon consideration of the embodiment descriptions provided below.

BRIEF DESCRIPTION OF THE DRAWINGS

FIG. 8 is a side view of a first portion of a slidable member of the implantation tool of FIG. 5.

FIG. 9 is a side view of a distal end portion of the first portion of the slidable member illustrated in FIG. 8.

DETAILED DESCRIPTION

Figure 1:
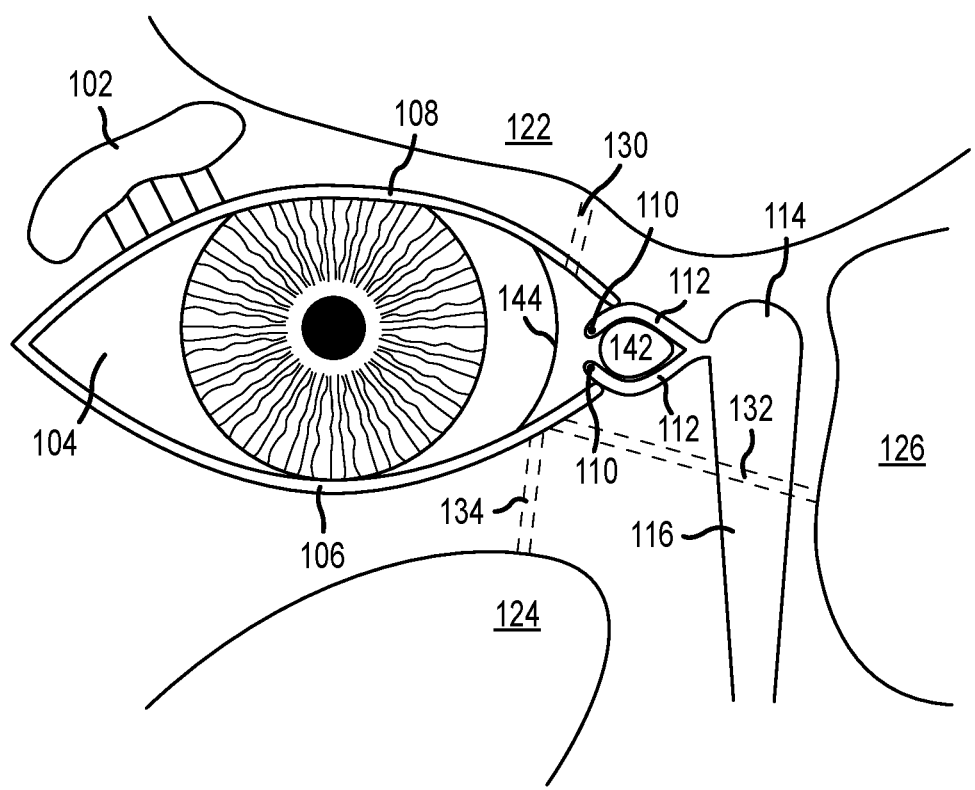
FIG. 1 is an illustration showing the lacrimal apparatus and some example routes for surgical paths between the lacrimal apparatus in the orbit and a paranasal sinus with a surgical approach through the palpebral fissure for implantation of an implant device to provide direct fluid communication access from the lacrimal apparatus in the orbit to the paranasal sinus.

The term "lacrimal apparatus" or "lacrimal system" refers to the collection of physiological components that accomplish the production and secretion of lacrimal fluid to lubricate the eyeball, containment of lacrimal fluid in a reservoir of lacrimal fluid in the orbit and drainage of lacrimal fluid from the orbit to the nasal cavity. The lacrimal apparatus includes the lacrimal glands, the tear drainage system and the reservoir of lacrimal fluid located between the lacrimal glands and the tear drainage system. The reservoir of lacrimal fluid includes the eyelid margins and the conjunctival sac (and including the pool of tears in the lower conjunctival cul-de-sac that is sometimes referred to as the lacrimal lake). The tear drainage system includes the puncta, canaliculi and nasolacrimal duct (including the so-called lacrimal sac located at the top of the nasolacrimal duct) through which excess tears drain to Hasner's valve and into the nasal cavity. FIG. 1 shows generally the lacrimal apparatus. Lacrimal fluid is produced and secreted from lacrimal glands 102 to lubricate the surface of the eyeball 104 disposed within the orbit. Lacrimal fluid forms a coating over the eyeball 104 and is generally contained within the conjunctival sac (the space between the lower eyelid 106, upper eyelid 108 and eyeball 104 that is lined by the conjunctiva). Excess lacrimal fluid is conducted to the vicinity of the medial canthus (medial corner of the eye) and drains through the lacrimal puncta 110 into the lacrimal canaliculi 112 and into the lacrimal sac 114 of the nasolacrimal duct 116. The lacrimal fluid then drains from the nasolacrimal duct 116 through Hasner's valve and into the nasal cavity.

As used herein, a surgical path refers to an artificially-created passage prepared by surgical means from an approach through the palpebral fissure between the lacrimal apparatus in the orbit and a paranasal sinus for implantation therethrough of an implant device with an internal passage to provide direct fluid communication access from the lacrimal apparatus in the orbit to the paranasal sinus. As may be appreciated, the palpebral fissure is an anatomical opening between eyelids, also referred to as the rima palpebrarum. Such an implant device may, for example, be of a design as described in any of U.S. Pat. Nos. 9,308,358; 9,561,350; U.S. Patent Application Publication No. 2017/0216094 A1 or International Patent Application Publication No. WO 2017/132573 A1, each of which is incorporated by reference herein.

The paranasal sinuses include the frontal sinuses, maxillary sinuses, ethmoid sinuses and sphenoid sinuses, which are cavities contained within frontal, maxilla, ethmoid and sphenoid bones, respectively. The paranasal sinuses drain into the nasal cavity. FIG. 1 also shows the general proximity of the frontal sinus 122, maxillary sinus 124 and ethmoid sinus 126 relative to features of the lacrimal apparatus and some example routes for a surgical path are shown by dashed lines. A first example route 130 for a surgical path is from the lacrimal apparatus in the orbit to the frontal sinus. A second example surgical path route 132 is from the lacrimal apparatus in the orbit to the ethmoid sinus 126. A third example surgical path route 134 is from the lacrimal apparatus in the orbit to the maxillary sinus 124. The example surgical path routes shown in FIG. 1 are for purposes of general illustration only and not to show precise locations where a surgical path might be formed to connect a part of the lacrimal apparatus with the corresponding paranasal sinus. Although not shown in FIG. 1, another example route for a surgical path is from the lacrimal apparatus in the orbit to the sphenoid sinus. One more specific example of a preferred route for a surgical path to a paranasal sinus is for the surgical path to pass directly through the lacrimal caruncle and through tissue to the targeted paranasal sinus. Such a route for a surgical path benefits from relatively easy location of the surgical entry point by a medical professional performing an implantation procedure.

Figure 2:
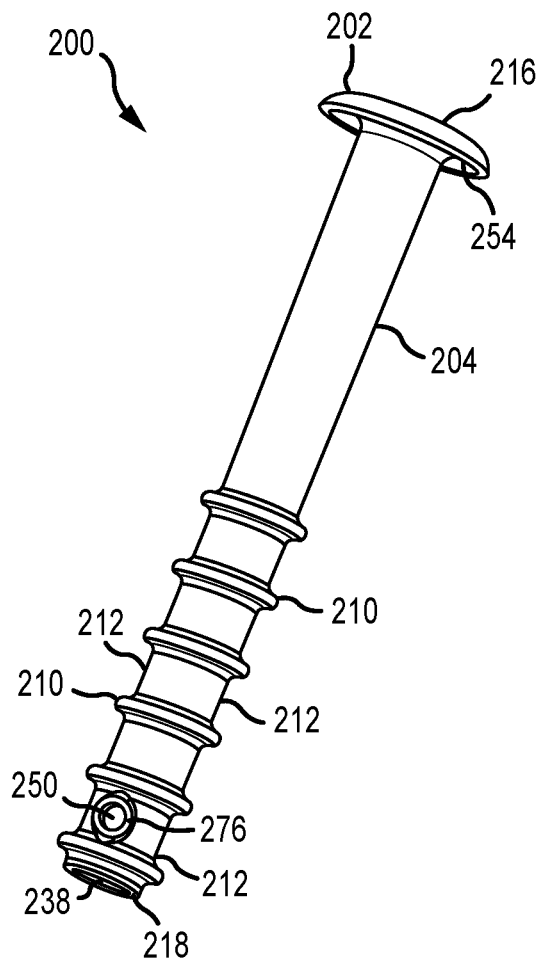
FIG. 2 is a perspective view of an example embodiment of a paranasal sinus access implant device for implantation to provide direct fluid communication access from the lacrimal apparatus in the orbit to the paranasal sinus.
Figure 3:
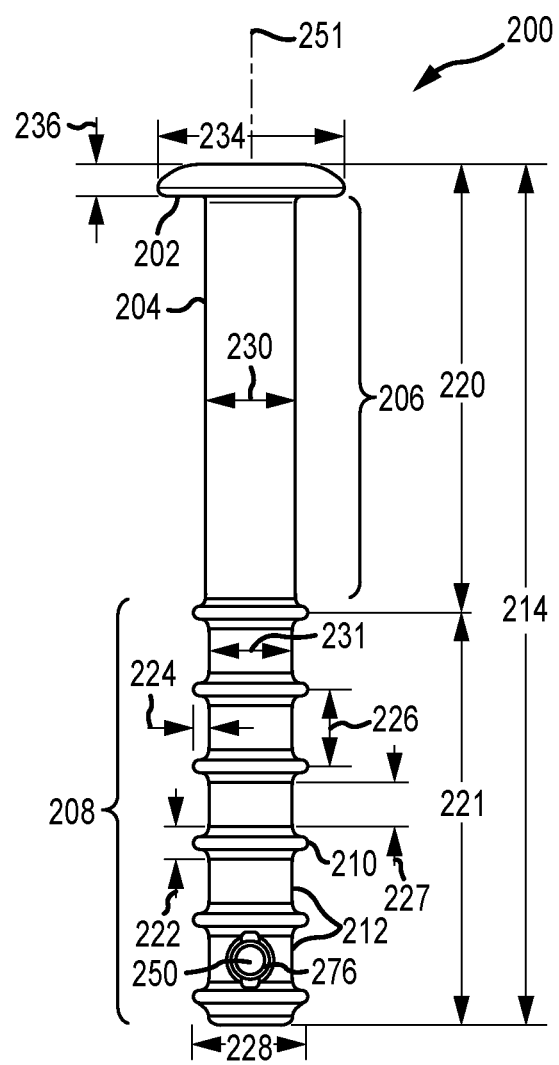
FIG. 3 is a side view of the paranasal sinus access implant device illustrated in FIG. 2.

FIGS. 2 and 3 show an example implant device 200 of a design as described in International Patent Application Publication No. WO 2017/132573 A1. The implant device 200 includes a head 202 and a conduit 204. The conduit 204 includes a first longitudinal portion 206 and a second longitudinal portion 208 disposed distal of the first longitudinal portion 206. The first longitudinal portion 206 includes a smooth exterior surface and second longitudinal portion 208 includes an anchoring surface feature including anchoring protrusions in the form of spaced circumferential ridges 210 and recess areas 212 between the ridges 210. When the implant device 200 is implanted through a surgical path to fluidly connect the lacrimal apparatus in the orbit with a paranasal sinus, one or more of the ridges 210 may be located in the vicinity of the paranasal sinus bone wall that is penetrated by the implant device 200 when implanted, preferably with one or more of the anchor protrusions disposed on each side of the bone, and more preferably with the wall of the sinus cavity bone penetrated by the implant device 200 disposed between two adjacent ones of the ridges 210. The implant device 200 includes an internal passage 238 extending between the proximal end 216 and the distal end 218, passing through the head 202 and the full length of the conduit 204. The internal passage 238 is open at the proximal end 216 for fluid communication with the lacrimal apparatus in the orbit when implanted and is open at the distal end 218 for fluid communication with a paranasal sinus when implanted, whereby the implant device 200 when implanted provides a fluid communication path between the lacrimal apparatus in the orbit and the paranasal sinus. Disposed between the most distal pair of adjacent ridges 210, the implant device 200 includes two side ports 250 disposed on opposite sides of a longitudinal axis 251 of the implant device 200, and which side ports are designed to be disposed in the paranasal sinus when the implant device 200 is implanted.

Various dimensions are shown in FIG. 3 for the implant device 200. The implant device 200 includes a length 214 measured longitudinally between the proximal end 216 and the distal end. The circumferential ridges 210 have a width 222 at the base of the ridges 210 and a height 224 above adjacent recess areas 212. The ridges 210 are spaced on a center-to-center spacing 226, with inter-ridge spacing 227 between adjacent bases of adjacent ridges 210. The conduit 204 has a maximum exterior width 228 corresponding with the tops of the ridges 210, equal to the diameter of the circle of the cross-section through the conduit 204 at the top of the ridges 210. The conduit 204 has a minimum exterior width 231 at locations corresponding with the recess areas 212 on the second longitudinal portion 208 of the conduit 204. The head 202 has a circular perimeter having a diameter 234 and a depth 236. The beginning, or proximal end, of the second longitudinal portion 208 is located at a distance 220 from the proximal end 216, at the base of the ridge 210 nearest to the proximal end 216 and the second longitudinal portion 208 has a length 221. The internal passage 238 has a circular cross-section along the length of the implant device 200, which is of constant diameter except that the diameter of the internal passage flares to a larger diameter in transition portions adjacent the proximal end 216 and the distal end 218, which are further described below.

Some example values for a number of the dimensions shown in FIG. 3 for one example embodiment of the implant device 200 are summarized in Table 1.

TABLE 1

| Dimension of Implant Device 200 | Specific Example |
|---|---|
| 214 | 17.8 mm |
| 220 | 8 mm |
| 221 | 8.9 mm |
| 222 | 0.44 mm |
| 224 | 0.3 mm |
| 226 | 1.65 mm |
| 227 | 1.21 mm |
| 228 | 2.41 mm |
| 230 | 2 mm |
| 231 | 1.8 mm |
| 234 | 4 mm |
| 236 | 0.9 mm |

Further features of the example implant device 200 are described in International Patent Application Publication No. WO 2017/132573 A1.

Figure 4:
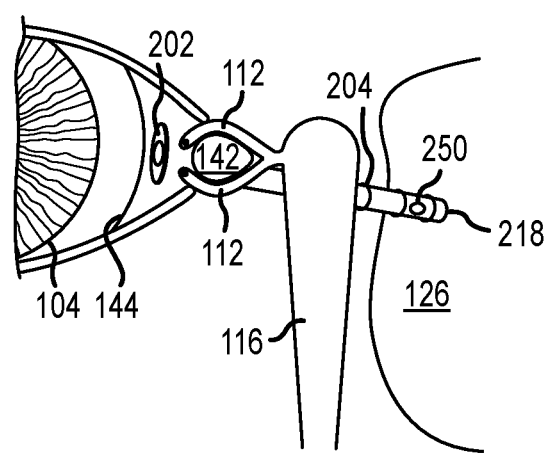
FIG. 4 is an illustration showing an example embodiment of a paranasal sinus access implant device in an implantation position as implanted to provide direct fluid communication access from the lacrimal apparatus in the orbit to an ethmoid sinus.

FIG. 4 shows an example of implant placement of the implant device 200 in an implantation position to fluid connect the lacrimal apparatus in the orbit with the ethmoid sinus. In the implantation position shown in FIG. 4, the head 202 and proximal end 216 are disposed in the lacrimal apparatus in the orbit in the conjunctival sac and the distal end 218 is disposed in the ethmoid sinus 126, with the conduit 204 passing through the surgical path across tissue including conjunctiva and a wall of the ethmoid bone in which the ethmoid sinus 126 is located, with some anchor ridges 210 disposed within the surgical path to engage tissue and help anchor the implant device 200, and with other ones of the anchor ridges 210 and the side ports 250 disposed in the ethmoid sinus. In an alternative example, the surgical path from the lacrimal apparatus in the orbit may pass directly through the lacrimal caruncle 142, and in the implantation position the head 202 may be disposed over and engage tissue of the lacrimal caruncle 142.

Whether the implanted implant design has a design of a type as illustrated in FIGS. 2 and 3 or a different design, after implantation, the implant device may be used to provide access to the paranasal sinus to perform medical procedures or treatments directed to the paranasal sinus, for example to administer a treatment composition (also referred to as a treatment formulation) the paranasal sinus or to aspirate fluid from the paranasal sinus. Such a treatment formulation may include one or more drugs for treatment of sinusitis or may be an irrigation fluid to irrigate the paranasal sinus.

With reference also to FIGS. 5-18, an embodiment of a paranasal sinus fluid access implantation tool 300 and various components of and example implantation procedures involving the implantation tool 300 will be described. For illustration purposes, the implantation tool 300 is shown in an implantation assembly with or being operated in connection with implantation of the example paranasal sinus fluid access implant device 200 shown in FIGS. 2-4.

Figure 5:
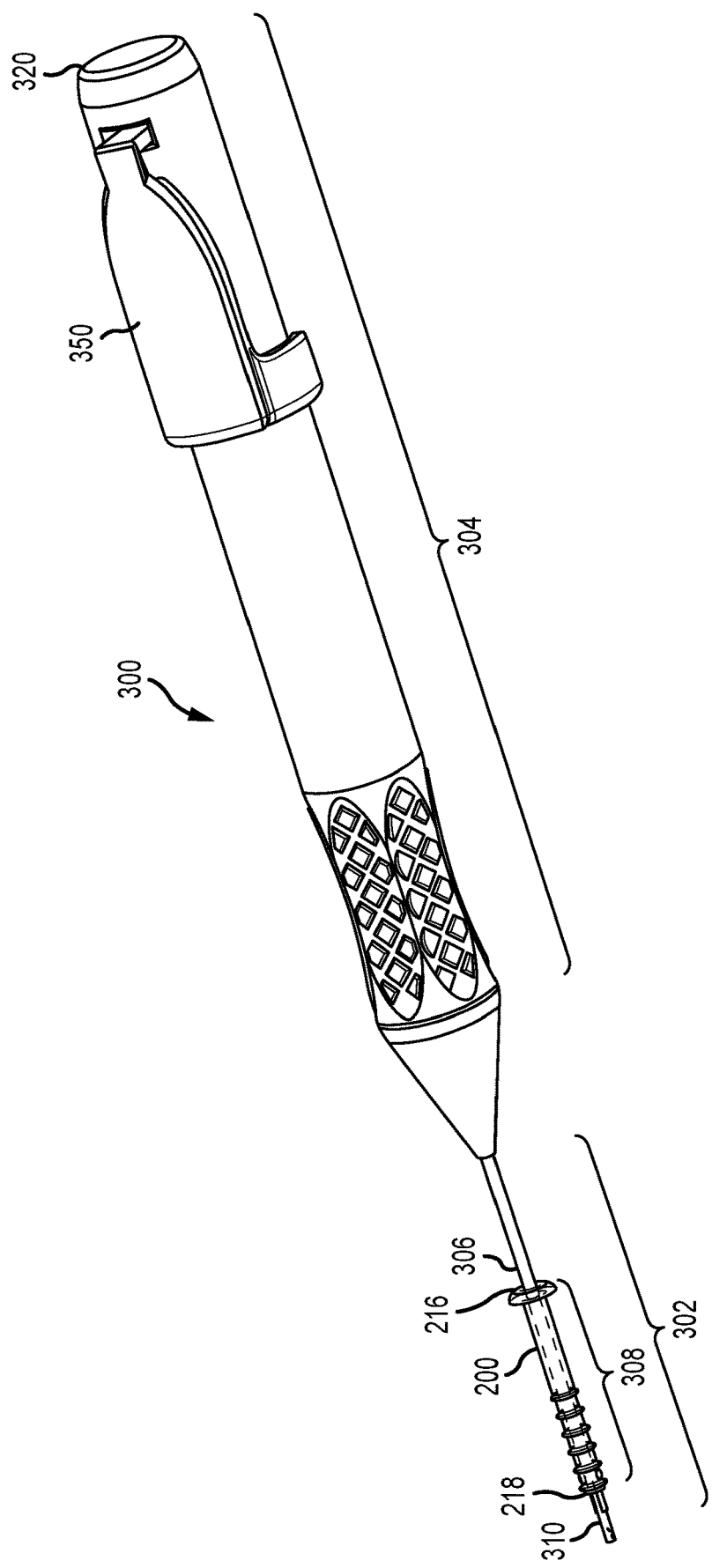
FIG. 5 is a perspective view showing an implantation assembly including an example embodiment of an implantation tool in an implantation assembly combination with an example paranasal sinus access implant device to be implanted using the implantation tool to provide direct fluid communication access from the lacrimal apparatus in the orbit to the paranasal sinus.
Figure 6:
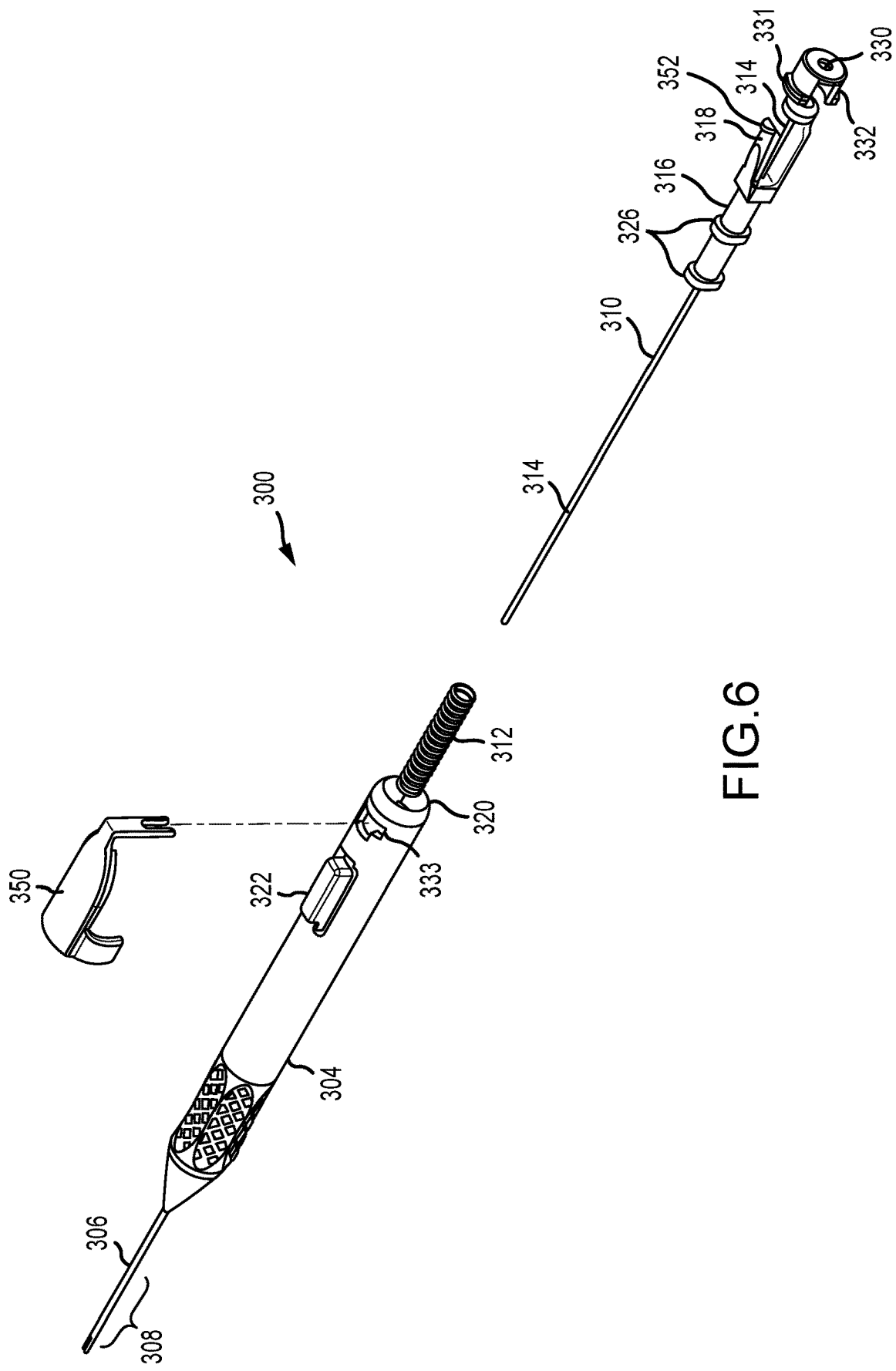
FIG. 6 is an exploded view showing components of the implantation tool of FIG. 5.
Figure 7:
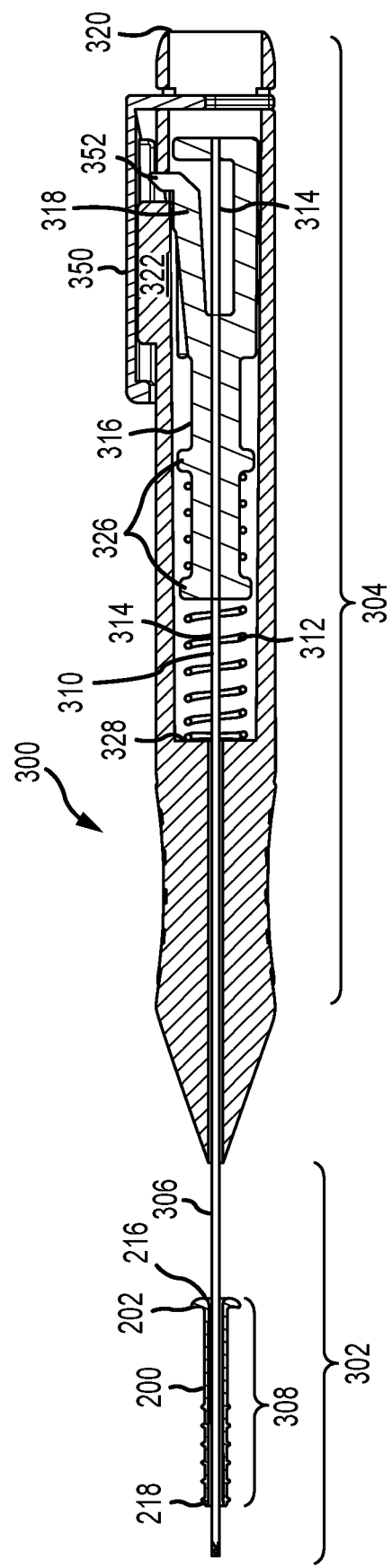
FIG. 7 is a sectional view taken along a section line along the length of the implantation tool of FIG. 5 in the implantation assembly configuration of FIG. 5 including the example paranasal sinus access implant device of FIG. 5.

The implantation tool 300 includes an insertion portion 302 configured to carry the implant device 200 for insertion through a surgical path between the lacrimal apparatus in the orbit and a paranasal sinus during an implantation procedure. The implantation tool 300 also includes a handle portion 304 configured to remain outside of the surgical path during the implantation procedure and which is manipulable by a medical practitioner to direct implantation of the implant device 200 during the implantation procedure. The insertion portion 302 includes a carrier member 306 on which the implant device 200 may be mounted to be carried to an implantation position through the surgical path from an approach through the palpebral fissure during an implantation procedure. The carrier member 306 includes a mounting portion 308. The mounting portion 308 is a longitudinal portion of the carrier member 306 on which the implant device 200 is secured to be carried by the carrier member 306 during an implantation procedure. As illustrated in FIGS. 5 and 7, the mounting portion 308 of the carrier member 306 corresponds with the length of the carrier member 306 along which the implant device 200 is secured to be carried by the implantation tool 300 during an implantation procedure. In this regard, a distal end of the mounting portion 308 may correspond with the distal end 218 of the implant device 200 and the proximal end of the mounting portion 308 may correspond with the proximal end 216 of the implant device 200 as the implant device 200 is secured to the carrier member 306 for an implantation procedure. It is noted that although the implant device 200 is mounted on and secured to such a mounting portion 308 of the carrier member 306 in preparation for an implantation procedure, when the implant device 200 is inserted on the carrier member 306 into the surgical passage during an implantation procedure, the implant device 200 may deform or shift somewhat relative to the carrier member 306, which may include a movement of some portion or portions of the implant device 200 along the carrier member 306 outside of the mounting portion 308, on which the implant device 200 was initially confined as initially mounted. For instance, with the implantation tool 300, only a distal portion the implant device 200 is secured to the carrier member 306, so that portions of the implant device 200 located proximal to the locations of securement will be in tension as the implant device 200 is inserted into and advanced through the surgical path for implant placement. This advantageously permits the implant device 200 to stretch out and elongate along the carrier member 306 proximal of the securement locations, and proximal portions of the stretched implant device 200 may extend proximal of the mounting portion 308 of the carrier member 306. Likewise, the secured distal portion of the implant device 200 may deform and shift position slightly around the locations of securement, which may slightly shift the positioning of the distal end 218 of the implant device 200 relative to the distal end of the mounting portion 308 of the carrier member 306.

As shown in FIGS. 5-17, a slidable member 310 is disposed mostly in internal working space housed within the handle portion 304 and the carrier member 306. The slidable member 310 is slidable along a translation path within the internal working space, and a spring 312 may provide a force to propel the slidable member 310 to release the implant device 200 from securement to the carrier member 306 to deploy the implant device 200 for implantation after the implant device 200 has been advanced in a surgical path to an implantation position. As shown in the figures, the slidable member 310 includes a first portion 314 in the form of an elongated conduit (e.g., hypodermic tube, also referred to as a hypo tube). The slidable member also includes a second portion 316 to interact with the spring 312 and has a depressable member 318 that may be depressed by a medical professional during an implantation procedure to release the spring 312 from a charged state (pre-compressed state) to propel the slidable member 310 toward a proximal end 320 of the implantation tool 300 to retract the slidable member 310 within the internal working space to release the implant device 200 from securement to the carrier member 306 for implantation deployment. The depressable member 318 interfaces with an actuation member in the form of an actuation button 322, which may be pushed by a medical professional to depress the depressable member 318 to actuate release of the implant device 200 from securement to the carrier member 306 during an implantation procedure. By way of example, the first portion 314 of the slidable member 310 may be in the form of a small diameter hypo tube (e.g., of stainless steel) and the second portion 316 of the slidable member 310 may be a plastic structure (e.g., of polypropylene) molded over the hypo tube.

Figure 10:
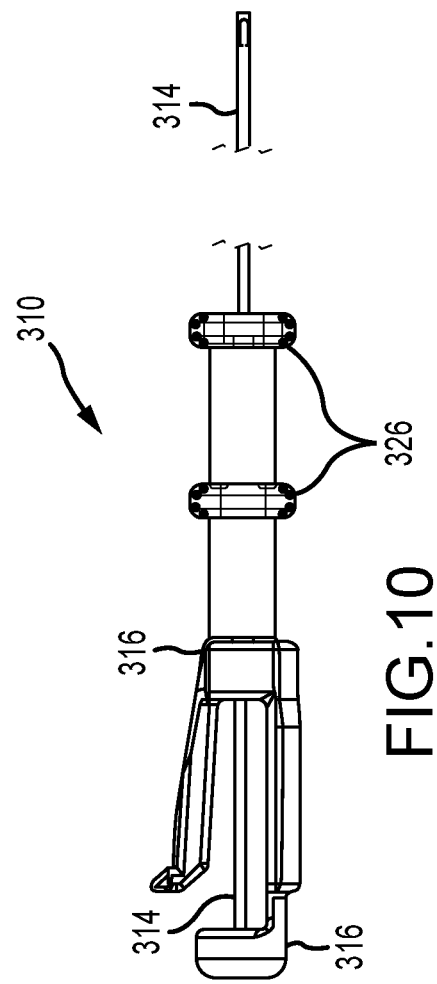
FIG. 10 is a side view of the slidable member of the implantation tool of FIG. 5.
Figure 11:
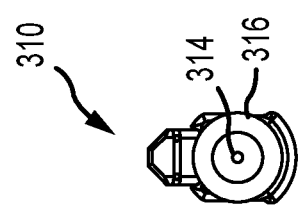
FIG. 11 is an end view of the slidable member shown in FIG. 10.

FIG. 8 illustrates the first portion 314 of the slidable member 310 in the form of a hypo tube with a flared proximal end 324 for more secure engagement with the over-molded second portion 316 of the slidable member 310, as illustrated in FIGS. 10 and 11. The second portion 316 of the slidable member 310 includes retaining projections 326 to engage and retain the spring 312 relative to the slidable member 310. In the example of the implantation tool 300, the actuation button 322 is part of a molded handle body piece (e.g., of polypropylene). In a compressed state, a distal end of the spring 312 is disposed against a shoulder feature 328 in the handle body. The implantation tool 300 includes a lumen provided through the first portion 314 of the slidable member 310 for passage of a guide wire therethrough to guide a distal end of the implantation tool 300 to the surgical path during an implantation procedure. The lumen is accessible from the proximal end 320 of the implantation tool 300 through an opening 330 though an end-cap insert 332 with tab portions 331 that lock into a proximal portion of an opening feature 333 in the handle body. The end-cap insert 332 encloses the internal working space adjacent the proximal end 320 and acts as a stop for movement of the slidable member 310 when propelled toward the proximal end 320 when the spring 312 in a compressed state is released by depression of the depressable member 318 through manipulation of the actuation button 322.

Figure 12:
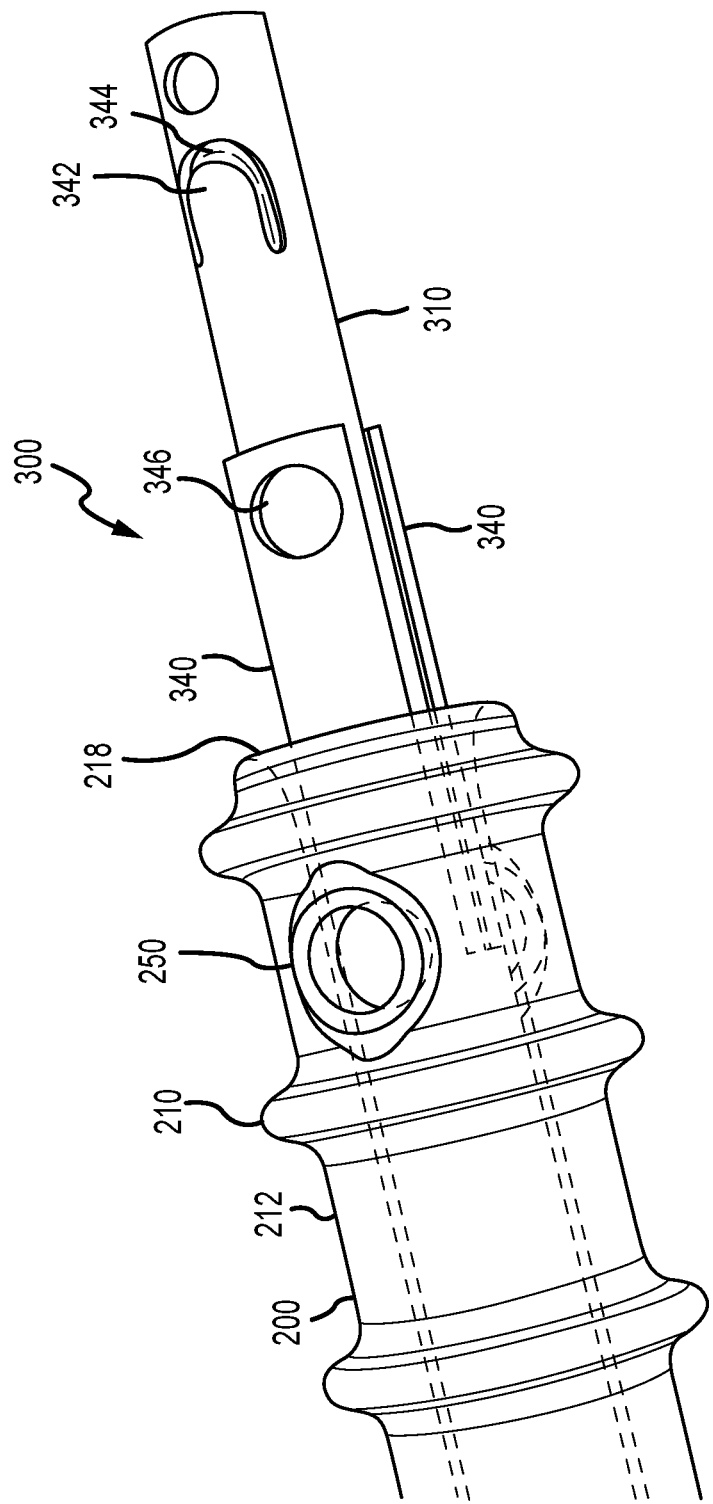
FIG. 12 is a perspective view of a distal end portion of the tool assembly combination shown in FIG. 5.
Figure 15:
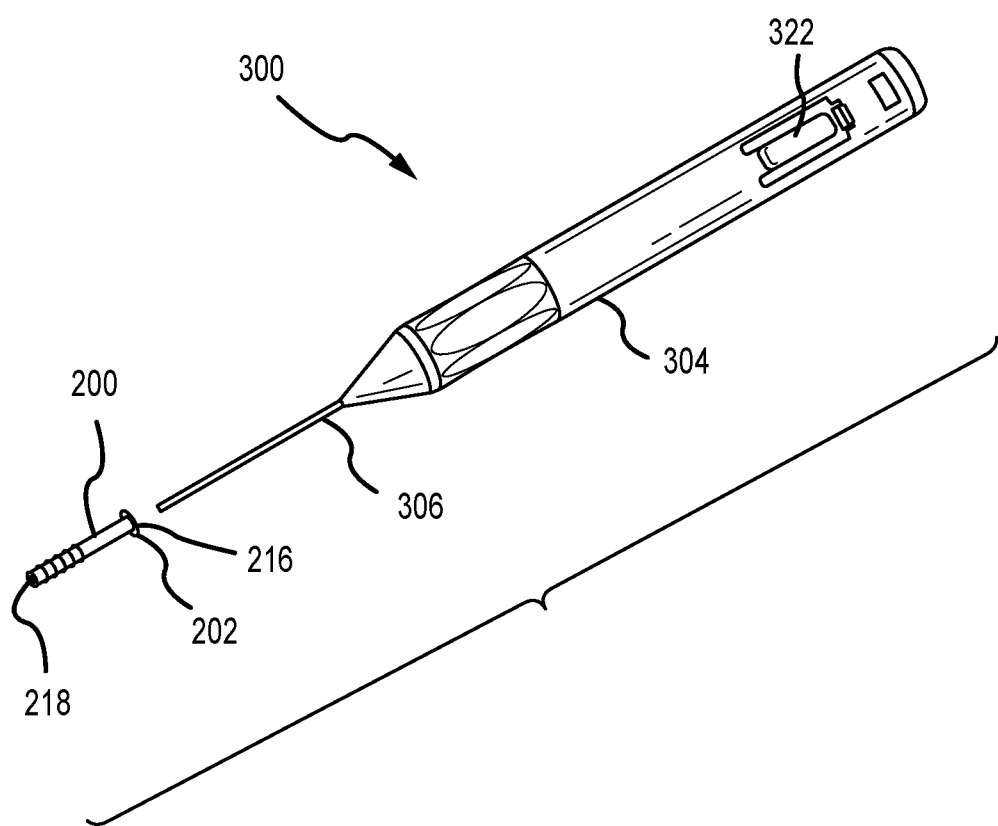
Figure 16:
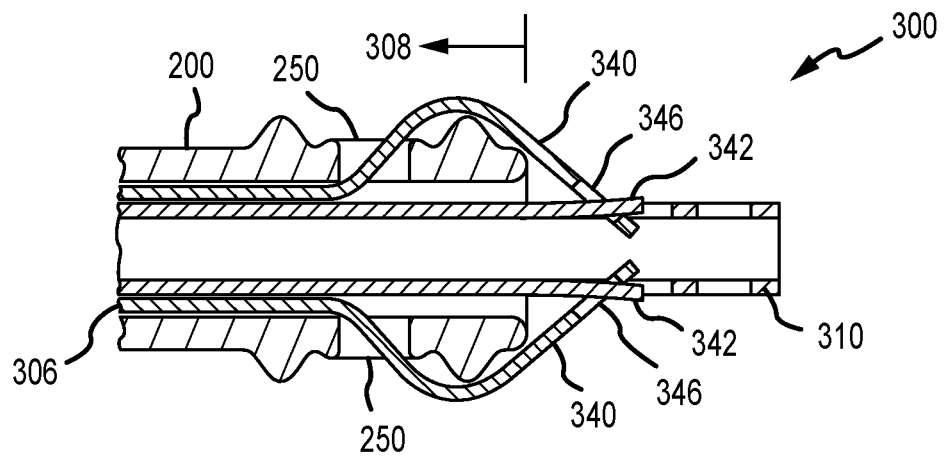
FIGS. 16-18 are partial sectional views illustrating a distal end portion of the implantation tool and the example embodiment of a paranasal sinus access implant device shown in FIG. 5 during an implantation procedure.

A key feature of the implantation tool 300 is a securement mechanism provided to secure the implant device 200 in an implantation orientation on the carrier member 306 to carry the implant device 200 to an implantation position through the surgical path during an implantation procedure. The securement mechanism is reconfigurable from a securement configuration to secure the implant device 200 to the carrier member 306 to a released configuration to release the implant device 200 from securement to the carrier member 306 after being advanced through a surgical path to an implantation position, permitting withdrawal of the implantation tool 300, and the carrier member 306, to disengage the carrier member 306 from the positioned implant device 200 to leave the implant device 200 in place for implantation. In the embodiment illustrated for the implant tool 300, the securement mechanism includes two securement members in the form of sheath members 340 that are integral with and provided as extensions at a distal end of the carrier member 306. In one example contemplated implementation, the carrier member 306 may be made of a polymeric composition with material properties permitting the integral sheath members 340 to be sufficiently ductile to be routed through the distally-located side ports 250 of the implant device 200 from inside of to outside of the side ports 250 and then distally over distal portions of the exterior of the implant device 200 to engage and be retained in a secured configuration by retainment structure features provided on distal end portions of the slidable members 310. As seen in FIGS. 8, 9 and 12, a distal end portion of the slidable member 310 includes securement tabs 342 cut into the wall of opposing sides of the distal end portion of the first portion 314 of the slidable member 310. Each of the securement tabs 342 is defined by a slot 344 cut through the wall of the first portion 314 of the slidable member 310 so that each securement tab 342 is configured be received through a corresponding opening 346 through a corresponding distal end portion of a sheath member 340 for securement of a sheath members 340 to the distal end portion of the slidable member 310. This permits the distal end portion of each sheath member 340 to be hooked over a corresponding securement tab 342 with the securement tab 342 projecting through the opening 346 of the sheath member 340 to hold the sheath member 340 secured in place in a securement configuration for advancement of the implant device 200 mounted on the carrier member 306 into and through a surgical route during an implantation procedure. An example of the engagement between the sheath members 340 and corresponding ones of the securement tabs 342 projecting through the openings 346 in an implantation assembly reading for an implantation procedure is illustrated for example, in FIG. 16. The secured sheath members 340 in the securement configuration engaged with the securement tabs 342 both secure the implant device 200 in an implantation orientation mounted on the carrier member 306 and provide a sheath-like protection of distal end portions of the implant device 200 that are covered by the sheath members 340, facilitating insertion of the implant device 200 into a surgical path and advancing the implant device 200 through the surgical path to an implantation position with reduced resistance to advancement from the distal end edge of the implant device 200. Securement of the implant device 200 to the carrier member 306 only at locations at and distal to the side ports 250 results in a majority of the length of the implant device 200 located proximal to the side ports 250 that is advanced into and through the surgical path to be advanced in a state of tension as a result of resistance to advancement from tissue in the surgical path pulling on the exterior of the conduit 204 of the implant device 200 when the implant device 200 is advanced through the surgical path, until the head 202 of the implant device 200 engages conjunctival tissue adjacent to the proximal opening of the surgical path when the implant device 200 has been fully advanced to an implantation position. As shown in FIG. 16, the mounting portion 308 of the carrier member 306 extends to the distal end of the implant device 200, with a distal end portion of the carrier member 306 extending along an exterior of the implant device 200 to the distal end of the implant device 200. In the embodiment of the implantation tool 300, the securement members in the form of the sheath members 340 are integral portions of the carrier member 306, which together with the distal end portion of the slidable member 310 including the tab portions 342 are part of a securement mechanism to secure the implant device in the implantation orientation on the carrier member 306. Is should be appreciated that the term "carrier member" as used herein refers to a carrying structure, which may be a combination of pieces or parts that during an implantation procedure provide the carrying function with the implant device mounted in a supported manner for advancing the implant device to an implantation position relative to a surgical path during an implantation procedure. In some alternative configurations to the implantation tool 300 as illustrated in FIGS. 5-18, one or more sheath members may extend out of the end of the internal passage of an implant device and fold back over the distal end of the implant device to extend over an exterior of a distal end portion of the implant device. For example, such a folded-over sheath member may be retained along a distal end portion of the implant device 200 by a snare-type structure, for example similar to as described below with respect to FIGS. 19-28, or by retainment features on a slidable member disposed in the vicinity of the side ports 250 of the implant device 200. In other alternative configurations, sheath members may be separate from a carrier member, and not an integral part of a carrier member.

Figure 17:
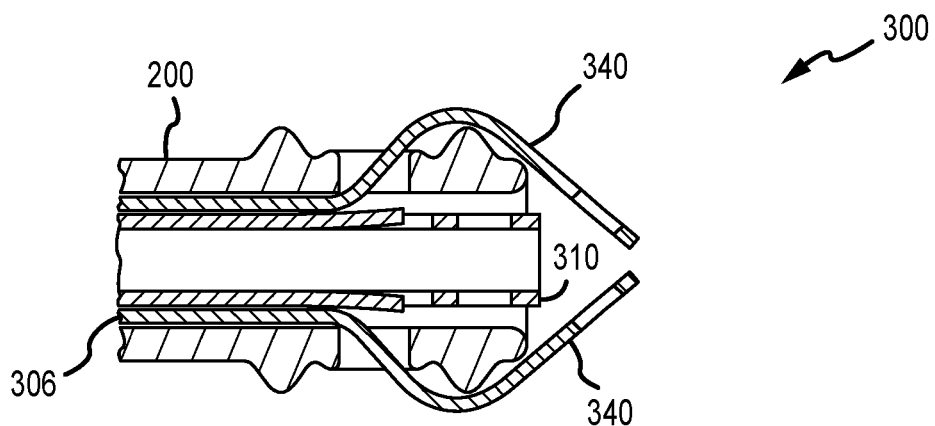

The implantation tool 300 includes a safety cover 350 attached to the handle body to cover the actuation button 322 to prevent hand access to the actuation button 322 to prevent premature release of the implant device 200 from securement to the carrier member 306 during an implantation procedure. When the implant device 200 has been positioned through a surgical path in an implantation position and ready to be released from securement to the carrier member 306 for implantation, the safety cover 350 may be selectively removed from the handle body by pulling up on the safety cover 350, thereby permitting hand access to the actuation button 322 to permit a medical practitioner to press the actuation button 322 to depress the depressable member 318 and to disengage a proximal projection 352 on the depressable member 318 from a corresponding recess feature in the handle body, as seen best in FIG. 7. As shown in FIG. 7, when the projection 352 is received in the corresponding recess feature in the handle body, the depressable member 318 is in a locked configuration maintaining the spring 312 in a compressed state. When the actuation button 322 is pushed down after removal from of the safety cover 350, the projection 352 is moved out of the locked configuration to permit expansion of the spring 312 from the compressed state to propel the slidable member 310 toward the proximal end 320 of the implantation tool 300, resulting in disengagement of the securement tabs 342 from the sheath members 340 to release the sheath members 340 from securing the implant device 200 to the carrier member 306. As the slidable member 310 moves toward the proximal end 300, a distal portion of the slidable member 310 is retracted into the interior working space within the carrier member 306, for example as illustrated in FIG. 17.

Figure 13:
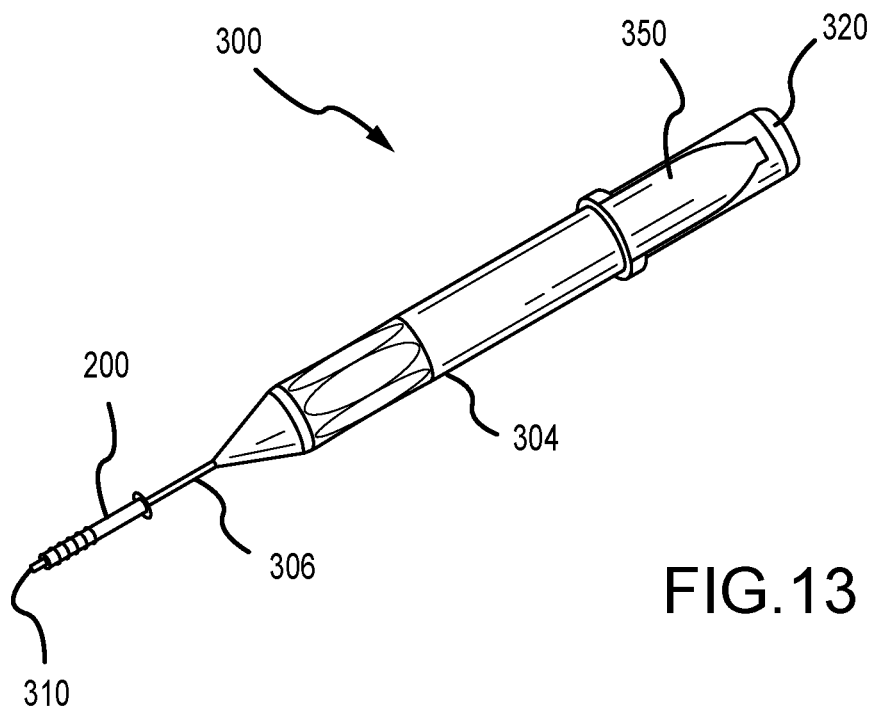
FIGS. 13-15 are perspective views illustrating use of the implantation tool shown in FIG. 5 during an implantation procedure to implant the example embodiment of a paranasal sinus access implant device shown in FIG. 5.
Figure 14:
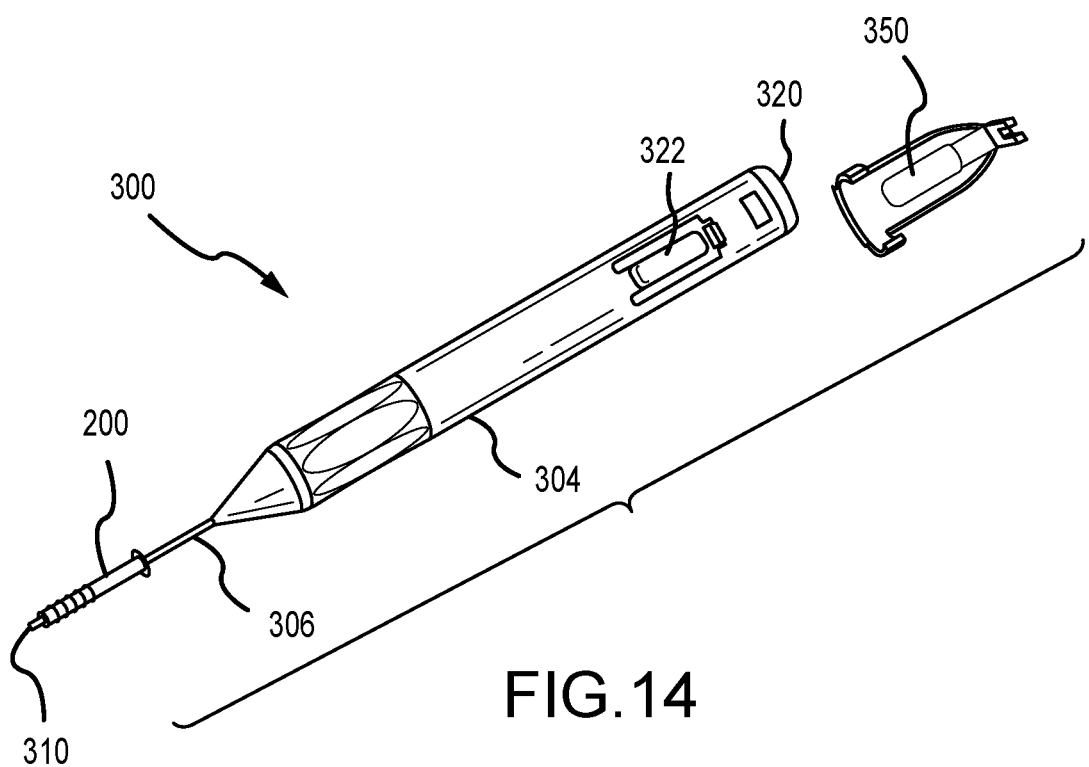
Figure 18:
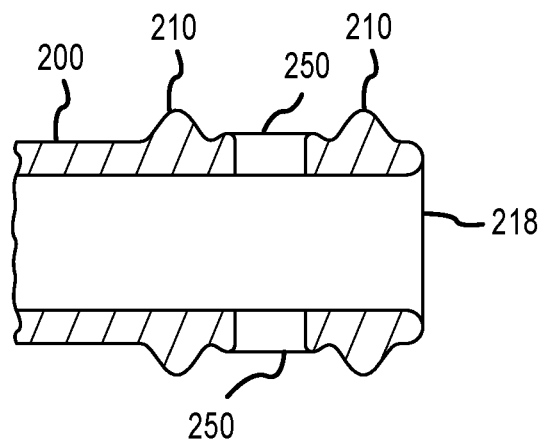

With continued reference primarily to FIGS. 5-18, performance of an example implantation procedure will be described using the implantation tool 300. FIG. 13 illustrates an implantation assembly ready for performing an implantation procedure with the implant device 200 mounted in an implantation orientation and secured to the carrier member 306. FIG. 16 illustrates a distal portion of the implantation tool 300 with the implant device 200 secured to the carrier member 306 by the sheath members 340 engaged with the securement tabs 342 on the first portion 314 of the slidable member 310, with the securement tabs 342 received through the openings 346 and the corresponding sheath members 340. As illustrated in FIG. 16, the securement tabs 342 may be slightly flared outward to enhance performance of the securement tabs 342 both for securing the sheath members 344 insertion into the surgical path and for release of the sheath members 340 when the tool member slidable member 310 is retracted to disengage from the sheath members 340 and to release the implant device 200 from securement to the carrier member 306. FIG. 14 illustrates actuation of the implantation tool 300 to reconfigure the securement mechanism from the securement configuration to the released configuration during an implantation procedure after the implant device 200 has been advanced into a surgical path to an implantation position with the distal end 218 disposed in a paranasal sinus (e.g., ethmoid sinus, maxillary sinus or frontal sinus) and with the proximal end 216 disposed in the lacrimal apparatus in the orbit, and preferably with a distal side of the head 202 in contact with conjunctival tissue in the orbit. Such an implantation position for the implant device 200 may be as illustrated for example in FIG. 4, but with the implant device 200 still secured to the carrier member 306 of the implantation tool 300. As shown in FIG. 14, with the implant device 200 in the implantation position through the surgical path, the safety cover 350 may be removed to permit access to the actuation button 322, which may be pushed to reconfigure the securement mechanism of the implantation tool 300 to the released configuration in which the implant device 200 is released from securement to the carrier member 306, as illustrated in FIG. 17. After the actuation button 322 has been pressed to release the implant device 200 from securement to the carrier member 306, a medical professional performing an implantation procedure may pull back on the handle portion 304 to withdraw the carrier member 306 from the surgical path to leave the implant device 200 in place implanted in the implantation position to fluidly connect a paranasal sinus with the lacrimal apparatus in the orbit, as shown in FIG. 15. As the carrier member 306 is being withdrawn relative to the implant device 200, the distal portions of the sheath members 340 are retracted through the side ports 250 of the implant device 200 leaving the implant device 200 implanted in the implantation position completely disengaged from the implantation tool 300, as shown in FIGS. 15 and 18, which may be in the implantation position as illustrated in FIG. 4.

The carrier member 306 of the implantation tool 300 may be made of a uniform material of construction throughout, or may be made of a first material of construction (e.g., metallic or hard engineering plastic material) with higher rigidity to carry the implant device 200 and a second material of construction for the sheath members 340 with a lower rigidity that is sufficiently malleable to be readily deformed to be passed through the side ports 250 and to engage with the securement tabs 342. Because of the support provided to the carrier member 306 by the slidable member 310 (e.g., made of stainless steel or another hard, rigid material) disposed through the carrier member 306, the entire carrier member 306, including the integral sheath members 340, may be made of a uniform material with properties advantageously selected for performance of both the sheath members 342 and other portions of the carrier member 306 to carry the implant device during an implantation procedure. Some example materials that may be used as a single material of construction for the carrier member 306, including the integral sheath members 342, or that may be used for only the sheath members 340, include polyimide, polyamide (e.g., nylon), Mylar, PET (polyethylene terephthalate), FEP (fluorinated ethylene propylene), PTFE (polytetrafluoroethylene), nitinol suture, PVF (polyvinyl fluoride), composite polymer and silicone composite compositions. Some preferred compositions are polymeric compositions, such as polyimide, polyamide (e.g., nylon), Mylar, PET (polyethylene terephthalate), FEP (fluorinated ethylene propylene) and PTFE (polytetrafluoroethylene) compositions, with polyamide (e.g., nylon) compositions more preferred for some implementations. One example for particularly preferred materials of construction for the carrier member 306, including the integral sheath members 342, are thermoplastic elastomers, and preferably polyether block amide elastomers (PEBAs). Polymeric compositions, or polymeric matrix for composites with a polymeric matrix, for the carrier member, and preferably for PEBA materials, with or without integral sheath members, may in some implementations have a Shore D hardness in a range of 50 to 100, preferably 60-90 and more preferably 60-80. One useful group of such PEBA materials are the Pebax® compositions from Arkema, and preferably some of the harder Pebax® materials (e.g., with a Shore D hardness of 60 or larger). For example some Pebax® compositions have a Shore D hardness of around 72 and are especially useful. Another useful group of such thermoplastic elastomers are the Vestamid® E compositions from Evonik, and preferably some of the harder such materials (e.g., having a Shore D hardness of 60 or larger).

With reference also to FIGS. 19-28, another embodiment of a paranasal sinus fluid access implantation tool 400 and various components of an example implantation procedures involving the implantation tool 400 will be described. For illustration purposes, the implantation tool 400 is described for mounting and implanting the example paranasal sinus fluid access implant device 200 shown in FIGS. 2-4.

The implantation tool 400 includes an insertion portion 402 configured to carry the implant device 200 for insertion through a surgical path between the lacrimal apparatus in the orbit and a paranasal sinus during an implantation procedure. The implantation tool 400 also includes a handle portion 404 configured to remain outside of the surgical path during the implantation procedure in which is manipulable by a medical practitioner to direct implantation of the implant device 200 during the implantation procedure. The insertion portion 402 includes a carrier member 406 on which the implant device 200 may be mounted to be carried to an implantation position through the surgical path with an approach through the palpebral fissure during an implantation procedure. The carrier member 406 includes a mounting portion 408, which is a longitudinal portion of the carrier member 406 on which the implant device 200 is secured to be carried by the carrier member 406 during an implantation procedure. The mounting portion 408 generally corresponds with the length of the carrier member 406 along which the implant device 200 is secured to be carried by the implantation tool 400 during an implantation procedure. A distal end of the mounting portion 408 may correspond with the distal end 218 of the mounted implant device 200 and the proximal end of the mounting portion 408 may correspond with the proximal end 216 of the mounted implant device 200. Similar to the discussion above concerning the implantation tool 300, although the implant device 200 is mounted on and secured to such a mounting portion 408 of the carrier member 406 in preparation for an implantation procedure, when the implant device 200 is inserted on the carrier member 406 into a surgical passage during an implantation procedure, the implant device 200 may deform or shift somewhat relative to the carrier member 406, including possibly moving somewhat outside of the mounting portion 408 on which the implant device 200 was initially confined as initially mounted.

A handle body of the handle portion 404 and the carrier member 406 provide a housing for internal components disposed in internal space within the implantation tool 400. A slidable release member 410 is disposed in the internal working space within the handle portion 404 and the carrier member 406. The release member 410 is slidable along a translation path within the internal working space. The release member 410 is connected with a release pin 412 that is engaged with and retains a release spring 414. A proximal end of the release pin 412 is threaded into an end piece 416 located adjacent a proximal end 417 of the implantation tool. The end piece 416 is selectively manipulable by a medical professional during an implantation procedure to reconfigure a securement mechanism of the implantation tool 400 from a securement configuration to a released configuration to release the implant device 200 from securement to the carrier member 408 to permit the implantation tool 400 and the carrier member 406 to be withdrawn and disengaged from the implant device 200 to leave the implant device 200 implanted in an implantation position.

The implantation tool 400 includes a securement member in the form of a snare member 418 and an alignment member 420 to assist in properly positioning and aligning the implant device 200 adjacent to the mounting portion 408 of the mounting member 406 with a distal end portion of the implant device 200 disposed through a snare loop formed by the snare member 418 for securing the implant device 200 to the carrier member 406 in the secured configuration. The snare member 418 is configured to be retractable to retract the snare loop about a distal portion of the implant device 200 disposed along the mounting portion 408 of the carrier member 406 to secure the implant device 200 to the carrier member 406. The implantation tool 400 also includes a guide loop member 422 that provides a small diameter loop near a distal end 424 of the implantation tool 400 for receiving a guide wire therethrough to guide the distal and 424 of the implantation tool 400 to a surgical path during an implantation procedure. The interior working space of the carrier member 406 is enclosed at a distal end of the carrier member 406 by a spherical end piece 426. The carrier member 406 may, for example, be in the form of a metallic hypo tube (e.g., stainless steel hypo tube) with a small diameter metallic ball (e.g., stainless steel bearing ball) for the spherical end piece 426 attached to and enclosing a distal end of the hypo tube.

The carrier member 406 includes five side apertures disposed toward the distal end 424. Two apertures 428 on opposing sides of the carrier member 406 provide passages for the guide loop member to exit from the interior working space of the carrier member 406. From the apertures 428 the guide loop member 422 may extend in a proximal direction through the interior working space of the carrier member 406 and may be connected to the handle transition piece 436 at a distal end of the handle portion 404 to retain the guide member loop 422 in a fixed orientation with a desired small diameter loop open to receive a guide wire for guiding the carrier member 406 to a proximal end of the surgical path during an implantation procedure. An aperture 430 provides a passage for the alignment member to exit the interior working space of the carrier member 406. From the aperture 430, the alignment member 420 may extend in a proximal direction through the interior working space of the carrier member 406 and may be connected to a slidable loading member 438 disposed in the interior working space within the handle portion 404. Apertures 432 and 434 provide passages for the snare member to exit the interior working space of the carrier member 406. From the aperture 432, a first portion of the snare member 418 may extend in a proximal direction through the interior working space of the carrier member 406 and may be connected with the loading member 438. A second portion of the snare member 418 may be disposed in the interior working space of the carrier member 406 with an engagement portion of the snare member 418 in the form of an end loop 440 retained in the interior working space by a distal end portion of the release member 410 disposed through the end loop 440 when the snare member 418 is in the securement configuration to secure the implant device 200 to an exterior of the carrier member 406. The release member 410 disposed through the loop end 440 maintains the loop member 418 with a snare loop adjacent an exterior of the carrier member 406 extending between the aperture 432 and the aperture 434. However, in the released configuration, the release member 410 is retracted to disengage from the loop end 440 of the loop member 418 to release the snare loop and accordingly to release the implant device 200 from securement to the carrier member 406.

Figure 22:
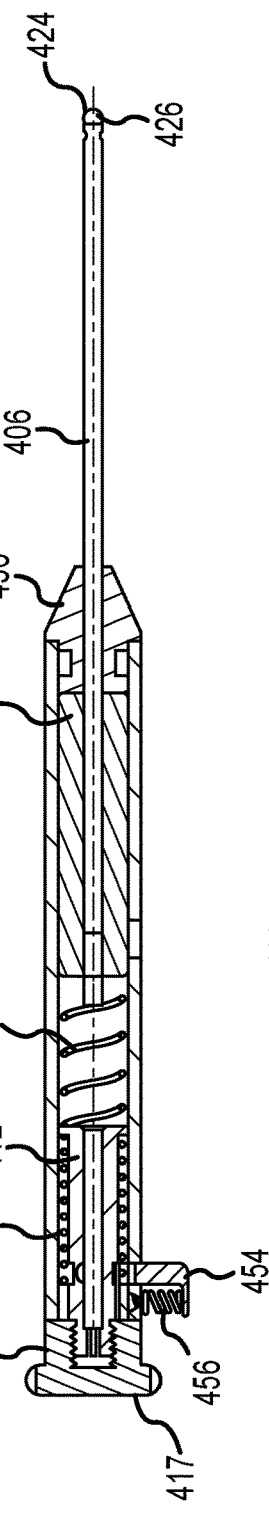
FIG. 22 is a sectional view of the implantation tool of FIG. 19 taken along a longitudinal section line as shown in FIG. 21.
Figure 24:
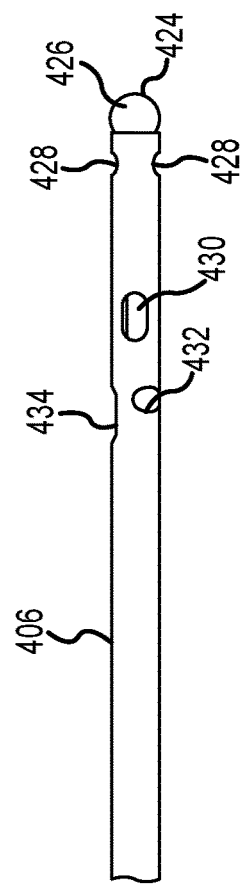
FIG. 24 is a partial side view of a distal end portion of a carrier member of the implantation tool of FIG. 19.
Figure 23:
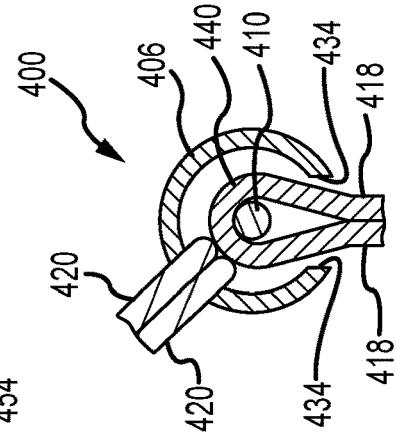
FIG. 23 is a partial sectional view of the implantation tool of FIG. 19 taken along a transverse section line as shown in FIG. 21.
Figure 25:
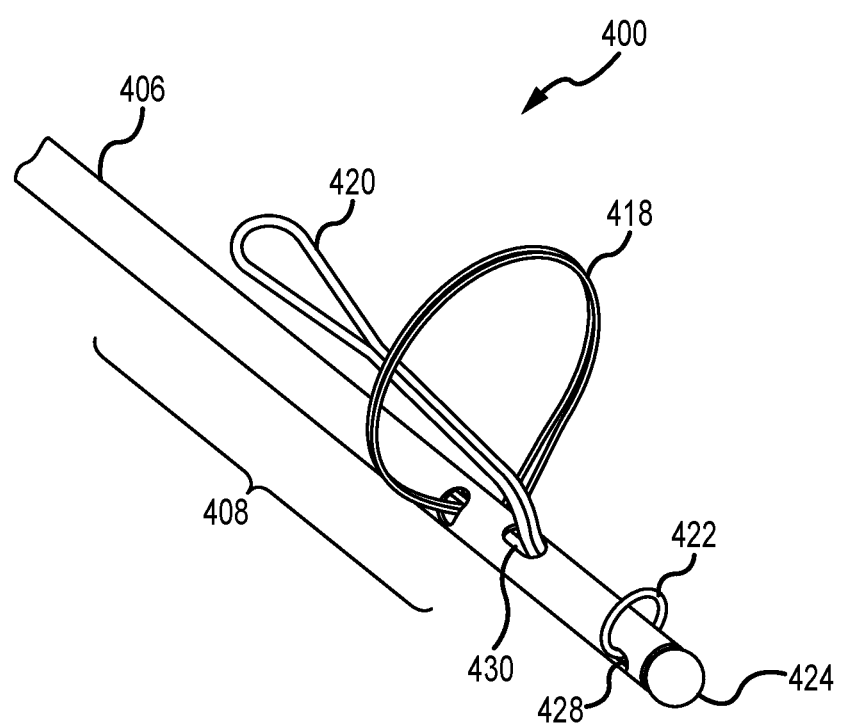
FIG. 25 is a perspective view of a distal end portion of the implantation tool of FIG. 19.

The snare member 418 may be disposed in three different configurations, referred to as a loading configuration, a securement configuration and a released configuration, respectively. In the loading configuration and the released configuration, the release pin 410 is disposed through the loop end 440 of the snare member 418 to maintain the snare member 418 with a snare loop extending between the aperture 432 and the aperture 434. In the loading configuration, the loading member 438 is in a forward position, as illustrated in FIGS. 22 and 23, and accordingly the end of the snare loop 418 connected to the loading member 438 is also in a forward position and the snare loop is in an expanded position to receive the implant device 200 to be secured to the mounting portion 408 of the carrier member 406. With the snare member 418 in the loading configuration, the implant device 200 may be guided to the proper position for securement to the carrier member 406 by inserting the alignment member 420 into the internal passage from the distal end 218 of the implant device 200 and sliding the implant device 200 over the alignment member 420 until the distal end 218 of the implant device 200 is stopped adjacent the aperture 434 by a bend portion of the alignment member 420 where the alignment member 420 exits the aperture 430. As fully advanced along the alignment member 420, a distal end portion of the implant device 200 will be disposed through and distal of the snare loop of the snare member 418. With the implant device 200 in such a position fully advanced along the alignment member 420, the snare member 418 may be repositioned to the securement configuration by a medical professional by retracting the loading member 438 along a translation path in the interior working space of the handle portion, resulting in retraction of the end of the snare member 418 connected to the loading member 438 to retract the snare loop of the snare member 418 to a retracted position around the distal end portion of the implant device 200 disposed through the snare loop 418. In the retracted position, the snare loop closes around the exterior of the implant device 200 and collapses the internal passage through the implant device 200 at the retracted snare loop location to firmly secure the implant device 200 to the mounting portion 408 of the carrier member 406. In contrast to the example implantation tool 300 in which the implant device 200 has the carrier member 306 disposed through the internal passage of the implant device 200 when the implant device 200 is secured to the carrier member 306, in the example implementation tool 400, the mounted implant device 200 is in the absence of the carrier member 406 disposed through the internal passage of the implant device 200 secured to the carrier member 406.

To reconfigure the snare member 418 from the loading configuration to the securement configuration, a medical professional may pull back on an actuation projection in the form of a knob member 446 connected with the loading member 438 with a portion of the knob member 446 disposed through and guided by a longitudinal portion of a slot track formed in a wall of a handle body providing a housing for components in the interior working space of the handle portion 404. As the knob member 446 is pulled back to retract the loading member 438, the loading member 438 compresses a loading spring 450 within the interior working space in the handle portion 404. When the knob member 446 has been pulled fully back to a retracted position at the end of the longitudinal portion of the slot track 448, the knob member may be translated in a transverse direction into a side portion 452 of the slot track 448 to lock the knob member 446 and the loading member 438 in a retracted position held securely in place by the force exerted by the compressed loading spring 450, thereby also maintaining the snare loop of the snare member 418 in the retracted position of the securement configuration. As the alignment member 420 is also connected to the loading member 438, as the loading member 438 is retracted, the alignment member 420 is also retracted with at least a portion of the alignment member being pulled into the interior working space of the carrier member 406, and including retracting into the interior working space a bend portion of the alignment member 420 that will make it easier for the alignment member 422 disengage from the implant device 200 during an implantation procedure after the implant device 200 has been released from securement to the carrier member 406. The alignment member may be made for example of a shape memory material, such as a nitinol material (nickel-titanium alloy), with shape memory for the bend portion. The snare member 418 may also be made of such a shape memory material with shape memory for the snare loop.

Figure 26:
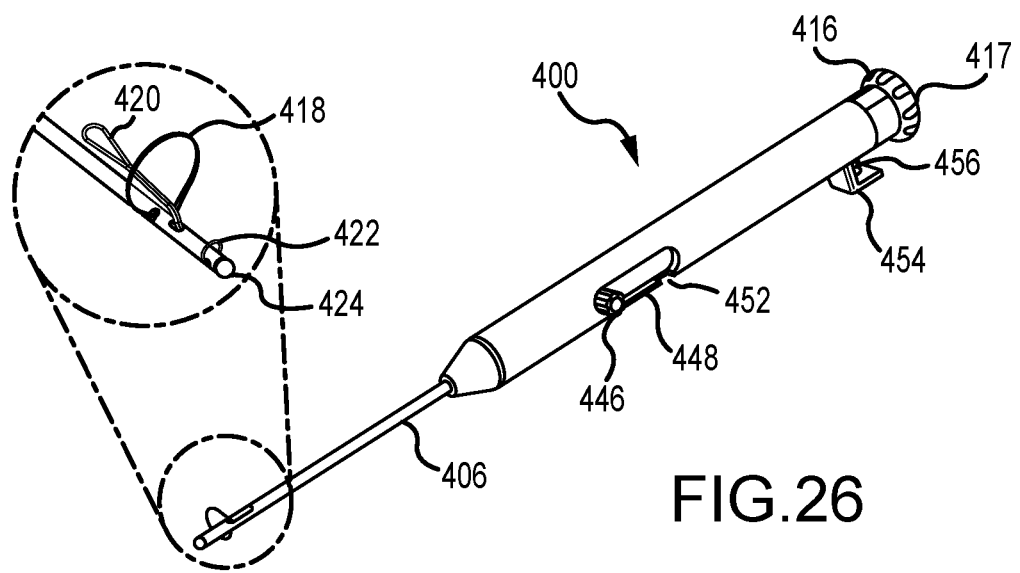
FIGS. 26-28 are perspective views illustrating use of the implantation tool of FIG. 19 in for performing an implantation procedure.
Figure 27:
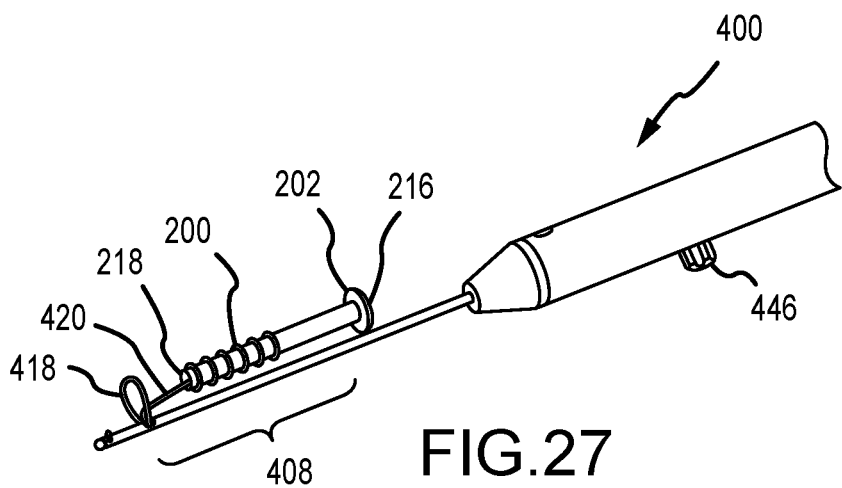
Figure 28:
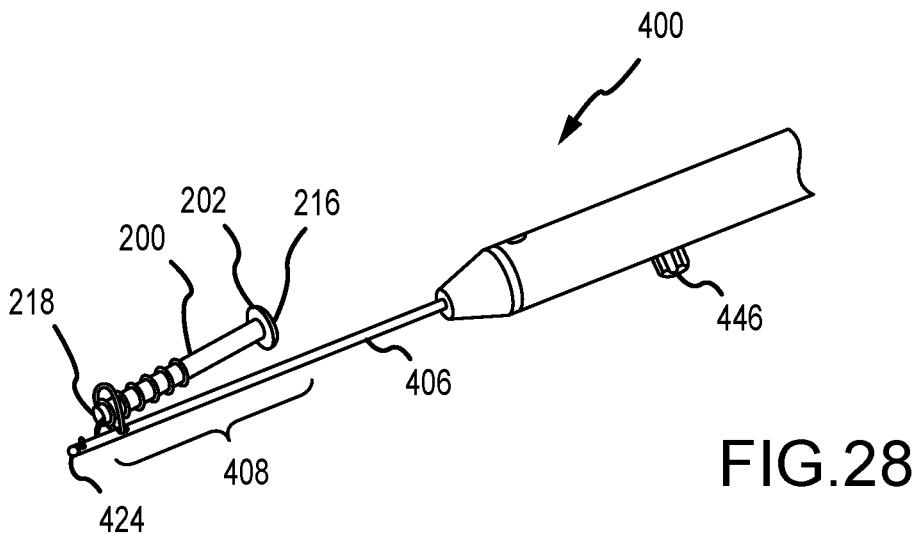

FIGS. 26-28 more particularly illustrate the process of mounting the implant device 200 on the mounting portion 408 of the carrier member 406. FIG. 26 shows the implantation tool 400 in the loading configuration ready to receive the implant device 200 for mounting. FIG. 27 shows sliding the implant device 200 over the alignment member 420 toward the snare loop of the snare member 418. FIG. 28 shows the implant device 200 fully advanced over the alignment member 420 into an implantation orientation for mounting on the mounting portion 408 of the carrier member 406. With the implant device 200 in the position as shown in FIG. 28, the knob member may be retracted along the longitudinal portion of the slot track 448 to retract the snare loop of the snare member 418 around a location on the distal end portion of the implant device 200 in the securement configuration. Preferably, the snare loop secures the implant device 200 to the carrier member at a securement location along the distal end portion of the implant device 200 that corresponds with a recess area 212 between anchor ridges 210, and preferably corresponds with the recess area 212 between the most distal pair of adjacent anchor ridges 210 (between which the side ports 250 are positioned in the example implant device 200). After the snare loop 418 is fully retracted around the implant device 200 to securely hold the implant device 200 to the carrier member 406, the knob member may be translated to the side into the side portion 452 of the slot track 448 to lock the snare member 418 in the securement configuration. With the implant device 200 secured to the carrier member in an implantation orientation, the carrier member 406 and the implant device 200 secured thereto may be advanced into a surgical path during an implantation procedure until the implant device 200 is advanced to an implantation position, preferably with the head 202 of the implant device 200 engaging tissue in the lacrimal apparatus in the orbit adjacent a proximal end of the surgical path. Once the implant device 200 is fully advanced to the implantation position, then the snare loop of the snare member 418 may be released to the released configuration for implantation of the implant device 200.

To reconfigure the snare member 418 from the securement configuration to the released configuration to release the implant device 200 from securement to the carrier member 406, the release member 410 may be retracted along a translation path within the interior working space of the implantation tool 400 by a medical professional pulling back on the end piece 416 to retract the release pin 412 and the release member 410 connected to the release pin 412, and to disengage the distal end portion of the release member 410 from the loop end 440 of the snare member 418. As the loop end 440 of the snare member 418 is released, the loop end 440 is no longer secured in the interior working space within the carrier member 406 and the snare loop is released, releasing the implant device 200 from securement to the carrier member 406, and permitting the implantation tool 400, and accordingly the carrier member 406 to be withdrawn from a surgical path relative to the implant device 200 to leave the implant device 200 implanted in an implantation position through the surgical path to fluidly connect the lacrimal apparatus in the orbit with a paranasal sinus.

Figure 19:
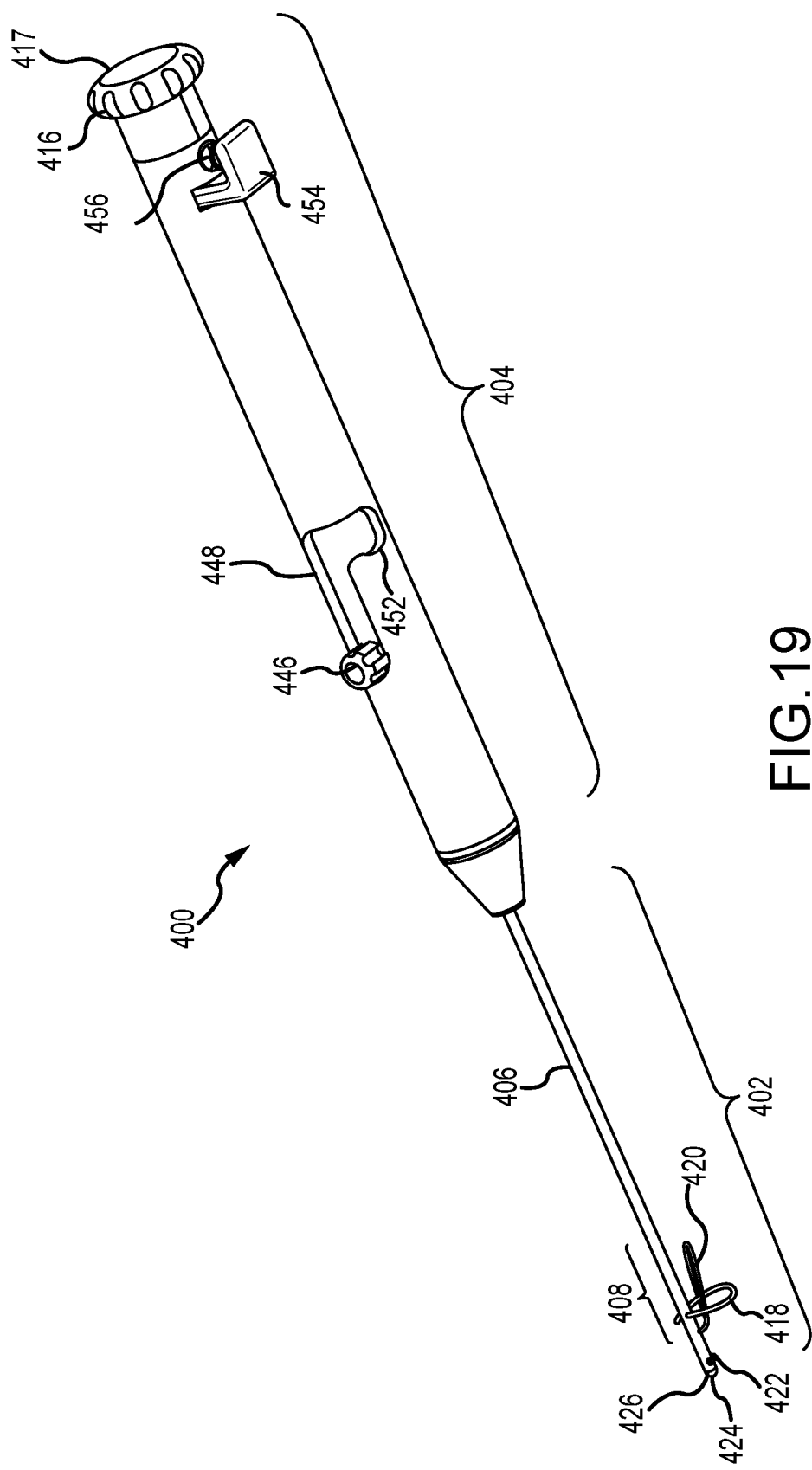
FIG. 19 is a perspective view showing another example embodiment an implantation tool for use to implant a paranasal sinus access implant device to provide direct fluid communication access from the lacrimal apparatus in the orbit to the paranasal sinus.
Figure 20:
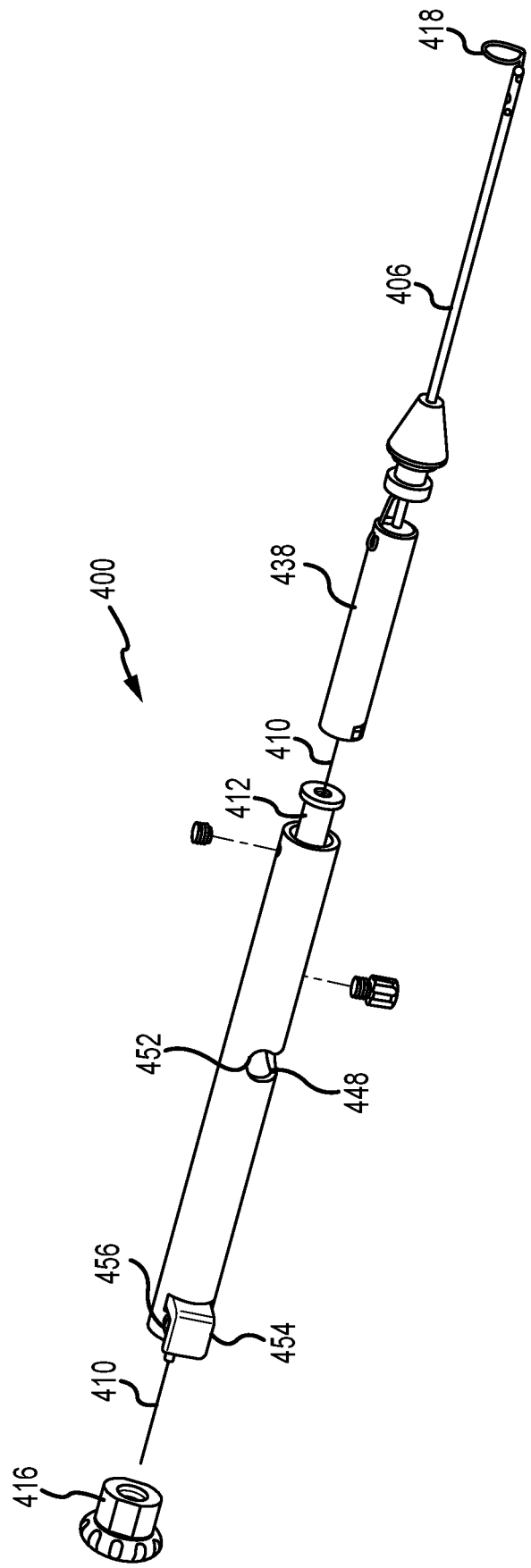
FIG. 20 is an exploded view showing components of the implantation tool of FIG. 19.
Figure 21:
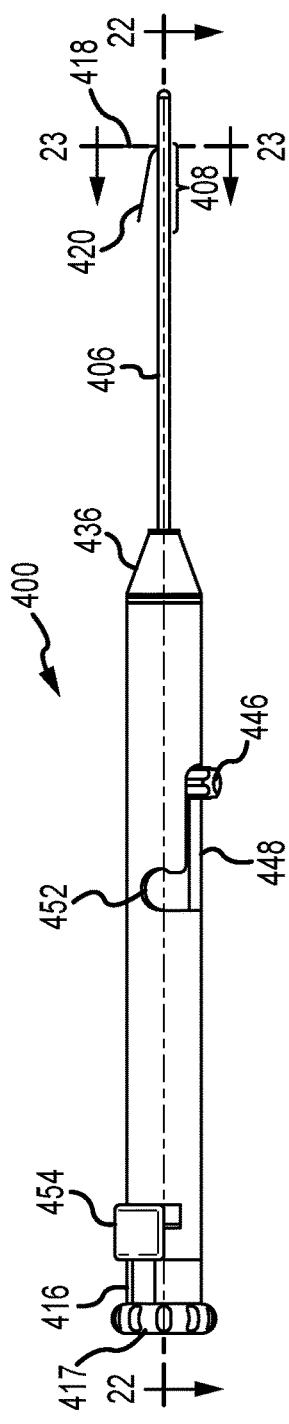
FIG. 21 is a top view of the implantation tool of FIG. 19.

The implantation tool 400 includes a lock member 454 that is normally maintained in a raised position as shown in FIGS. 19, 21 and 22 by a lock spring 456. In the raised position, the lock member 454 engages the release pin 412 to maintain the release pin 412 in a locked position to prevent premature retraction of the release pin 412 and the release member 410. Prior to pulling back on the end piece 416 to retract the release pin 412, the medical professional would depress the lock member 454 to unlock the release pin 412, and while holding the lock member 454 in the depressed position would pull back on the end piece 416 to retract the release pin 412 and the release member 410. The release spring 414 may initially be in an uncharged state or, preferably, in a charged extension state with the release spring 414 biasing the release pin 412 and the release member 410 toward the proximal end 417 of the implantation tool 400 and urging the end piece 416 toward the release pin 412, such that when a medical professional pulls back on the end piece 416, the medical professional must pull with sufficient force to overcome the biasing force of the release spring 414. As may be appreciated, in the configuration shown for the implantation tool 400 the release spring 414 and the loading spring 450 will be isolated from each other.

In alternative configurations to the configuration of the implantation tool 400 illustrated in FIGS. 19-28, an implantation tool with a snare-type securement structure of the type illustrated in FIGS. 19-28 may be adapted for mounting an implant device with the carrier member extending through the internal passage of the implant device and with a snare loop extending around at least circumferential portion of the exterior of the implant device, for example including alignment of snare exit apertures such as apertures 432 and 434 with features such as side ports 250 of the implant device 200.

IMPLEMENTATION COMBINATIONS

Some other contemplated embodiments of implementation combinations for various aspects of this disclosure, with or without additional features as disclosed above or elsewhere herein, are summarized in the exemplary combinations presented below:

1. An implantation tool to implant a paranasal sinus fluid access implant device with an internal fluid communication passage through an artificial, surgical path between a lacrimal apparatus in the orbit and a paranasal sinus in an implantation procedure to provide direct fluid communication access through the internal passage from the lacrimal apparatus in the orbit to the paranasal sinus, the implantation tool comprising:

a carrier member configured to carry the implant device on a mounting portion of the carrier member in a mounted orientation to position the implant device in an implantation position through the surgical path from an approach through the palpebral fissure during the implantation procedure;

a securement mechanism to secure the implant device in the implantation orientation on the carrier member to carry the implant device to the implantation position during the implantation procedure, the securement mechanism being reconfigurable from a securement configuration to secure the implant device to the mounting portion of the carrier member in the implantation orientation to a released configuration to release the implant device from securement to the carrier member to permit withdrawal of the carrier member relative to the implant device to leave the implant device implanted in the implantation position during the implantation procedure;

a handle portion connected with the carrier member and configured to remain outside of the surgical path during the implantation procedure and being manipulable by a medical practitioner to direct implantation of the implant device during the implantation procedure;

internal working space housed within at least a portion of the handle portion and at least a portion of the carrier member;

a release mechanism disposed at least in part in the internal working space and manipulable to reconfigure the securement mechanism from the securement configuration to the released configuration.

2. The implantation tool according to example combination 1, wherein the securement mechanism comprises at least one securement member positioned to extend over and press against an exterior portion of the implant device in the implantation orientation when the securement mechanism is in the securement configuration.

3. The implantation tool according to example combination 2, wherein the securement mechanism comprises at least two said securement members each positioned to extend over and press against a said exterior portion of the implant device when the securement mechanism is in the securement configuration.

4. The implantation tool according to either one of example combination 2 or example combination 3, wherein at least one said securement member extends from outside of to inside of the internal working space in the carrier member.

5. The implantation tool according to either one of example combination 2 or example combination 3, wherein at least one of said securement member extending distal to a distal end of the mounting portion of the carrier member in the securement configuration to cover a distal end portion of the implant device when mounted on the mounting portion in the implantation orientation.

6. The implantation tool according to example combination 5, comprising at least two said securement members each extends distal to a distal end of the mounting portion of the carrier member in the securement configuration, to cover a distal end portion of the implant device when mounted on the mounting portion in the implantation orientation.

7. The implantation tool according to any one of example combinations 2-6, wherein each said securement member is in tension in the securement configuration.

8. The implantation tool according to any one of example combinations 2-7, comprising a slidable member disposed at least in part in the internal working space in the carrier member, and the securement mechanism comprises a retainment structure on the slidable member to engage and retain a distal portion of at least one said securement member in the securement configuration.

9. The implantation tool according to example combination 8, comprising at least two said securement members, and wherein: the slidable member comprises at least two said retainment structures, each to engage and retain a said distal portion of a different said securement member in the securement configuration.

10, The implantation tool according to either one of example combination 8 or example combination 9, wherein the slidable member is in a first position when the securement mechanism is in the securement configuration and is in a second position when the securement mechanism is in the released configuration.

11. The implantation tool according to example combination 10, wherein the second position is slidably retracted toward a proximal end of the implantation tool relative to the first position.

12. The implantation tool according to either one of example combination 10 or example combination 11, wherein the release mechanism comprises a translation path within the internal working space in which at least a proximal portion of the slidable member is slidable when slidably repositioning the slidable member from the first position to the second position.

13. The implantation tool according to either one of example combination 11 or example combination 12, wherein the release mechanism comprises a spring mechanism in a charged state applying a biasing force to the slidable member when the slidable member is in at least one of the first position and the second position.

14, The implantation tool according to example combination 13, wherein the spring mechanism is in the charged state when the slidable member is in the first position with the biasing force directed to urging the slidable member toward the second position.

15. The implantation tool according to example combination 14, wherein the release mechanism comprises an actuator mechanism retained in a locked configuration maintaining the spring mechanism in the charged state with the slidable member in the first position, and wherein:

the actuator mechanism is hand manipulable to release the actuator mechanism from the locked configuration to release the spring mechanism from the charged state to propel the slidable member to the second position.

16. The implantation tool according to example combination 15, wherein the charged state is a compressed state, and the release of the actuator mechanism from the locked configuration permits expansion of the spring from the compressed state.

17. The implantation tool according to either one of example combination 15 or example combination 16, wherein the actuator mechanism comprises a movable actuation member that is hand movable to release the actuator mechanism from the locked configuration, and the implantation tool comprises a safety cover selectively movable to selectively cover and uncover the movable actuation member to permit and prevent hand access to the movable actuation member.

18. The implantation tool according to example combination 17, wherein the movable actuator member is a depressable member.

19. The implantation tool according to example combination 13, wherein the spring mechanism is in a charged state when the slidable member is in the first position with the biasing force directed to urging the slidable member toward the first position.

20. The implantation tool according to example combination 19, wherein release mechanism comprises and actuator mechanism that is hand-manipulable to apply a force to the spring mechanism to overcome the biasing force of the spring mechanism and move the slidable member to the second position against the biasing force.

21. The implantation tool according to example combination 20, wherein the charged state is an extended state and when the slidable member is in the second position the spring mechanism is in a more extended state than in the first position.

22. The implantation tool according to any one of example combinations 8-21, wherein the slidable member has a lumen therethrough configured for passage therethrough of a guide wire to guide a distal end of the implantation tool to the surgical path during an implantation procedure.

23. The implantation tool according to any one of example combinations 8-22, wherein a said retainment structure and a distal portion of a securement member engaged with a said retainment structure in the securement configuration are disposed distal of a distal end of the mounting portion of the carrier member, and optionally distal of a distal end of the implant device in the implantation orientation when the securement mechanism is in the securement configuration.

24. The implantation tool according to example combination 23, wherein each said retainment structure and each said distal portion of a securement member engaged with a said retainment structure in the securement configuration are disposed distal of a distal end of the mounting portion of the carrier member.

25. The implantation tool according to example combination any one of example combinations 8-24, wherein a said retainment structure and a said distal portion of a said securement member engaged with a said retainment structure in the securement configuration are disposed distal of a distal end of the internal working space in the carrier member.

26. The implantation tool according to example combination 25, wherein each said retainment structure and each said distal portion of a securement member engaged with a said retainment structure in the securement configuration are disposed distal of a distal end of the internal working space in the carrier member.

27. The implantation tool according to any one of example combinations 2-26, wherein at least one said securement member is configured to extend from inside the interior passage of a said implant device mounted in the implantation orientation on the implant portion of the carrier member, through a side port of the said implant device to outside of the said implant device, from the side port over a said exterior portion of the implant device to a distal end of the implant device and distal to the distal end of the said implant device.

28. The implantation tool according to example combination 27, wherein at least two said securement members are each configured to extend from inside the interior passage of a said implant device mounted in the implantation orientation on the implant portion of the carrier member, through a different said side port of the said implant device to outside of the said implant device, from the said side port over a said exterior portion of the implant device to a said distal end of the implant device and distal to the said distal end of the said implant device.

29. The implantation tool according to either one of example combination 27 or example combination 28, wherein each said securement member configured to extend through a said side port has a maximum cross-dimension in a range of from 0.55 millimeter to 0.85 millimeter.

30. The implantation tool according to any one of example combinations 2-23, wherein a said securement member comprises a snare member retained in a snare loop to press against an exterior portion of a portion of a said implant device received through the snare loop when the securement mechanism is in the securement configuration.

31. The implantation tool according to example combination 30, wherein the snare member is released from the snare loop when the securement mechanism is in the released configuration.

32. The implantation tool according to any one of example combinations 2-29, wherein at least one said securement member comprises a sheath member configured to extend over a distal end of the implant device in the implantation orientation when the securement mechanism is in the securement configuration; and the sheath member is configured to cover a radial portion of a circumference around the distal end of the implant device in the implantation orientation when the securement mechanism is in the securement configuration, and optionally the radial portion is at least 20°.

33. The implantation tool according to example combination 32, wherein at least two said securement members each comprises a said sheath member, with each said sheath member configured to extend over a different said radial portion of the distal end of the implant device when the securement mechanism is in the securement configuration; and optionally, each said radial portion is at least 30°.

34. The implant tool according to either one of example combination 32 or example combination 33, wherein each said radial portion is not larger than 120°.

35. The implantation tool according to any one of example combinations 2-34, wherein each said securement member is configured to contact a said exterior portion of a said implant device positioned in the implantation orientation relative to the mounting portion of the carrier member not more than 5 millimeters proximal of a distal end of the implant device in the implantation orientation when the securement mechanism is in the securement configuration.

36. The implantation tool according to any one of example combinations 1-35, wherein the mounting portion of the carrier member is configured with a length along the carrier member between a proximal end and a distal end of the carrier member, wherein a distal end of the mounting portion corresponds with a mounted positioning of a distal end of a said implant device in the implantation orientation in the securement configuration and a proximal end of the mounting portion corresponds with a mounted positioning of a proximal end of the said implant device in the implantation orientation in the securement configuration.

37. The implantation tool according to example combinations 1-36, wherein the length of the mounting portion of the carrier member is in a range of from 8 millimeters to 45 millimeters. Optionally the range may have a lower limit of 8 millimeters, 10 millimeters, 12 millimeters or 15 millimeters and an upper limit of 45 millimeters, 35 millimeters, 30 millimeters or 25 millimeters.

38. The implantation tool according to any one of example combinations 1-37, comprising an internal passage extending through the implantation tool from the handle portion to adjacent a distal end of the implantation tool for passing a guide wire through the implantation tool to distal of the distal end of the implantation tool, to guide the distal end of the carrier member to the surgical path during the implantation procedure.

39. The implantation tool according to example combination 38, wherein the internal passage extending through the implantation tool comprises a central lumen through the implantation tool.

40. The implantation tool according to any one of example combinations 1-39, wherein the carrier member has a cross-section at a proximal end of the mounting portion with a maximum cross-dimension of the cross section in a range of from 0.7 to 1.2 millimeters; and optionally the carrier has a constant cross-section with the maximum cross-dimension for at least 5 millimeters along a length of the mounting portion from the proximal end of the mounting portion and further optionally along the entire length of the mounting portion.

42. The implantation tool according to example combination 40, wherein the carrier member has the cross-section for at least 5 millimeters along the length of the carrier member proximal of the mounting portion 43. The implantation tool according to any one of example combinations 1-42, comprising the snare member of either one of example combination 30 or example combination 31, and wherein in the securement configuration the snare loop in the retracted position has a maximum cross-dimension across the snare loop in a range of from 0.5 millimeter to 1.5 millimeters, and optionally with the range having a lower limit of 0.5 millimeter, 0.6 millimeter or 0.7 millimeter and an upper limit of 1.5 millimeters, 1.3 millimeter or 1.1 millimeter.

44. The implantation tool according to any one of example combinations 30, 31 and 43, wherein:

the handle portion is manipulable to reposition the snare member between a loading configuration and the securement configuration; and in the loading configuration the snare loop is in an expanded position to receive the implant device prior to retracting the snare loop to the retracted position to secure the implant device relative to the mounting portion of the carrier member.

45. The implantation tool according to example combination 44, wherein in the loading configuration the snare loop in the expanded position has a maximum cross-dimension across the snare loop in a range of from 1 millimeter to 5 millimeters larger than the maximum cross-dimension in the retracted position, and optionally the range having a lower limit of 1 millimeter, 1.5 millimeters or 2 millimeters and an upper limit of 5 millimeters, 4 millimeters or 3.5 millimeters.

46. The implantation tool according to either one of example combination 44 or example combination 45 comprising an alignment member, wherein when the snare member is in the loading configuration with the snare loop in the expanded position:

the alignment member is disposed through the snare loop and is configured to be inserted through the internal passage of the implant device to guide the implant device into a loading position to be secured to the exterior of the carrier member in the implantation orientation when the snare member is repositioned from the loading configuration to the securement configuration; and the alignment member has a free insertion end to be inserted into a proximal end of the internal passage to guide the implant device to the loading position, the free insertion end being disposed along the exterior of carrier member proximal of the snare loop.

47. The implantation tool according to example combination 46, wherein when the snare member is in the loading configuration with the snare loop in the expanded position, the implantation tool includes an insertion stop to limit a distance of insertion travel of the alignment member through the internal passage and locate the distal end of the implant device for the loading position.

48. The implantation tool according to any one of example combinations 44-47, comprising:

the internal working space extending through at least a portion of the handle portion and the carrier member in a longitudinal direction from the proximal end toward the distal end of the implantation tool; and a retractor manipulable through the handle portion to selectively reconfigure the snare loop from the loading configuration to the securement configuration, wherein the retractor comprises a retraction member disposed in the internal working space and connected with the snare member, the retraction member being selectively retractable within the internal working space toward the proximal end of the implantation tool through manipulation of the handle portion to retract a portion of the snare member connected with the retraction member during reconfiguration of the snare member from the loading configuration to the securement configuration.

49. The implantation tool according to Example combination 48, wherein the retractor comprises a spring with at least a portion disposed in the internal working space proximal the retraction member and positioned in the internal working space to be compressed when the retraction member is retracted toward the proximal end of the implantation tool during reconfiguration of the snare member from the loading configuration to the securement configuration.

50. The implantation tool according to example combination 49, wherein the handle portion comprises:
a housing portion with a slot track, the slot track having a longitudinal portion extending in a longitudinal direction along the handle portion and a side portion extending transverse to the longitudinal portion; and
a hand-manipulable actuation projection connected with the retraction member and projecting from the slot track to outside of the housing portion, the actuation projection being slidable along the longitudinal portion of the slot track to retract the retraction member from a forward position disposed toward the distal end of the implant device when the snare member is in the loading configuration to a retracted position disposed toward the proximal end of the implant device relative to the forward position, and at the retracted position the actuation projection being translatable in a transverse direction into the side portion of the slot track to lock the retraction member in place biased forward by the compressed spring to retain the snare member locked in the securement configuration.

51. The implantation tool according to example combination 50, wherein the longitudinal portion of the slot track has a length in a direction of a longitudinal axis of the implantation tool in a range of from 10 millimeters to 15 millimeters.

52. The implantation tool according to any one of example combinations 49-52, comprising the alignment member of either one of example combination 46 or example combination 47, and wherein the alignment member is connected with the retraction member and at least a portion of the alignment member is retracted into the internal working space within the carrier member when the retraction member is retracted during reconfiguration of the snare member from the loading configuration to the securement configuration.

53. The implantation tool according to example combination 52, wherein as the snare member is reconfigured from the loading configuration to the securement configuration, the alignment member is retracted to be entirely disposed within the internal working space.

54. The implantation tool according to either one of example combination 52 or example combination 53, wherein when the snare member is in the loading configuration the alignment member extends from inside the internal working space to outside of the carrier member through a side aperture of the carrier member.

55. The implantation tool according to any one of example combinations 43-54, comprising a loop release member extending through at least a portion of the internal working space in the carrier member, the loop release member being slidable within the internal working space between a first position engaged with an engagement portion of the snare member to maintain the snare member including a said snare loop and a second position disengaged from the engagement portion of the snare member to release the snare member from including a said snare loop; and wherein:
the release member is in the first position when the snare member is in the securement configuration and the release member is in the second position when the snare member is in the released configuration.

56. The implantation tool according to example combination 55, wherein the release member is connected with a release handle exposed on the handle portion of the implantation tool for hand-manipulation adjacent a proximal end of the implantation tool, wherein the release handle is manipulable to slide the release member in the internal working space from the first position to the second position to release the snare loop and reconfigure the snare member from the securement configuration to the released configuration.

57. The implantation tool according to example combination 56, comprising a release member spring biasing the release member into the first position when the snare member is in the securement position and wherein:
manipulation of the release handle to slide the release member from the first position to the second position counteracts a biasing force of the release spring.

58. The implantation tool according to any one of example combinations 55-57, wherein: the handle portion is manipulable to reposition the snare member between the loading configuration and the securement configuration according to any one of example combinations 44-54; and
the release member is retained in the first position when the snare member is in the loading configuration and while the snare member is reconfigured from the loading configuration to the securement configuration.

59. The implantation tool according to any one of example combinations 55-58, comprising a release lock manipulable through the handle portion between a locked configuration in which the release member is locked in the first position and an unlocked configuration in which the release member is unlocked and movable from the first position to the second position.

60. The implantation tool according to any one of example combinations 55-59, wherein the handle portion is manipulable to reposition the snare member between the loading configuration and the securement configuration according to any one of example combinations 44-54, and the implantation tool comprises the alignment member of either one of example combination 46 or example combination 47, and wherein the alignment member is connected with the release member and at least a portion of the alignment member is retracted into the internal working space within the carrier member when the release member is repositioned from the first position to the second position during reconfiguration of the snare member from the securement configuration to the released configuration.

61. The implantation tool according to example combination 60, wherein as the snare member is reconfigured from the securement configuration to the released configuration, the alignment member is retracted to be entirely disposed within the internal working space.

62. The implantation tool according to either one of example combination 60 or example combination 61, wherein when the snare member is in the loading configuration and when the snare member is in the securement configuration the alignment member extends from inside the internal working space to outside of the carrier member through a side aperture of the carrier member.

63. The implantation tool according to any one of example combinations 43-62, wherein the snare member has a cross-dimension along all of the snare member in a said snare loop in a range of from 0.05 millimeters to 0.5 millimeters.

64. The implantation tool according to any one of example combinations 43-63, comprising the alignment member according to any one of example combinations 46, 47, 52, 53 and 60-62, wherein the alignment member is constructed of a material selected from the group consisting of nitinol, stainless steel, nylon, polyester, PVDF (polyvinylidene fluoride), polypropylene, and polyethylene.

65. The implantation tool according to any one of example combinations 43-64, wherein the snare loop in the retracted position is configured to retain the implant device to the exterior of the carrier member in the absence of the carrier member being disposed through the internal passage of the implant device.

66. The implantation tool according to example combination 65, wherein the handle portion is manipulable to reposition the snare member between a loading configuration and the securement configuration according to any one of example combinations 44-54; and the snare loop in the expanded position is configured to receive for insertion therethrough a distal portion of the implant device in the absence of the carrier member being disposed through the internal passage of the implant device.

67. The implantation tool according to any one of example combinations 1-66, wherein the carrier member has a length in a range of from 10 millimeters to 45 millimeters.

68. The implantation tool according to any one of example combinations 1-67, wherein the carrier member has a maximum cross-dimension in a range of from 0.7 millimeter to 1.2 millimeters proximal of the mounting portion of the carrier member, and optionally proximal of a distal end of the mounting portion.

69. The implantation tool according to any one of example combinations 1-68, wherein the implantation tool has a length in a range of from 100 millimeters to 150 millimeters.

70. An implantation assembly for implanting a paranasal sinus fluid access implant device through a surgical path between a lacrimal apparatus in the orbit and a paranasal sinus in an implantation procedure to provide direct fluid communication access from the lacrimal apparatus in the orbit to the paranasal sinus through an internal passage of the implant device, the implantation assembly comprising:

the implant device: and the implantation tool according to any one of example combinations 1-69, wherein the implant device is mounted in the mounting orientation on the mounting portion of the carrier member with the securement mechanism in the securement configuration.

71. The implantation assembly according to example combination 70, wherein the implant device is in the absence of the carrier member being disposed through the internal passage of the implant device.

72. The implantation assembly according to either one of example combination 70 or example combination 71, wherein the internal passage of the implant device is collapsed at a location of securement to the mounting portion of the carrier member by the securement mechanism.

73. The implantation assembly according to example combination 70, wherein the carrier member is disposed through the implant device.

74. The implantation assembly according to any one of example combinations 70-73, wherein a portion of the implant device in contact with the securement mechanism comprises a polymeric material of construction having a Shore A durometer in a range of from 50 to 100.

75. The implantation assembly according to example combination 74, wherein the implant device is constructed of polymeric material having a Shore A durometer in a range of from 50 to 100.

76. The implantation assembly according to any one of example combinations 70-75, wherein the securement mechanism secures the implant device to the carrier member at securement locations, and wherein none of the securement locations are disposed more than 5 millimeters proximal of a distal end of the implant device along the length of the carrier member.

77. The implantation assembly according to any one of example combinations 70-76, wherein the securement mechanism does not contact a said exterior of the implant device at any location on the implant device disposed more than 5 millimeters from a distal end of the implant device.

78. The implantation assembly according to any one of example combinations 70-77, wherein:

the implant device comprises an exterior anchor surface feature to anchor the implant device in tissue between the lacrimal apparatus in the orbit and the paranasal sinus, the exterior anchor surface feature comprising anchor protrusions configured to engage the tissue and recess areas between the anchor protrusions with anchor protrusions and recesses between anchor protrusions; and the securement mechanism contacts a said exterior of the implant device extending over at least one anchor protrusion.

79. The implantation assembly according to any one of example combinations 70-78, wherein:

the implant device has a length between a proximal end of the implant device and a distal end of the implant device; and the implant device includes an insertion portion configured to enter and be advanced by at least some distance through the surgical path during an implantation procedure, the insertion portion having a length portion in from the distal end along a length of the implant device toward the proximal end that is shorter than a length of the implant device.

80. An implantation kit for implanting a paranasal sinus fluid access implant device through a surgical path between a lacrimal apparatus in the orbit and a paranasal sinus in an implantation procedure to provide direct fluid communication access from the lacrimal apparatus in the orbit to the paranasal sinus through an internal passage of the implant device, the implantation kit comprising:

the implantation tool according to any one of example combinations 1-69; and the implant device;

wherein, the implantation tool and implant device are assembled or assemblable into the implantation assembly of any one of example combinations 70-79.

81. An implantation kit according to example combination 80, comprising a fluid treatment formulation contained in a fluid container, the fluid treatment formulation comprising at least fluid composition for administration to the paranasal sinus through the internal passage of the implant device following implantation to fluidly connect the lacrimal apparatus in the orbit with the paranasal sinus.

82 An implantation kit according to example combination 81, wherein the fluid treatment formulation comprises at least one drug for treatment of sinusitis.

83. An implantation kit according to example combination 82, wherein the fluid treatment formulation is an irrigation fluid to irrigate the paranasal sinus.

84. An implantation kit according to any one of example combinations 80-83, wherein the implantation assembly is according to example combination 79.

85. A method for implanting a paranasal sinus access implant device to fluidly connect a lacrimal apparatus in the orbit with a paranasal sinus, comprising:

with a surgical approach through the palpebral fissure, surgically forming an artificial surgical path between a location in a lacrimal apparatus in the orbit and a paranasal sinus;

advancing the implantation assembly of any one of example combinations 70-79 from an approach through the palpebral fissure until the implant device extends through the surgical path in the implantation position;

manipulating the release mechanism to reconfigure the securement mechanism from the securement configuration to the released configuration;

withdrawing the implantation tool from the surgical path, leaving the implant device implanted through the surgical path fluidly connecting the lacrimal apparatus in the orbit with the paranasal sinus.

86. The method according to example combination 85, comprising after the withdrawing, administering a fluid treatment formulation to the paranasal sinus through the internal passage of the implanted implant device.

87. The method according to either one of example combination 85 or example combination 86, wherein the implantation assembly is according to example combination 79.

88. A method for implanting a paranasal sinus fluid access implant device through an artificial, surgical path between a lacrimal apparatus in the orbit and a paranasal sinus to provide direct fluid communication access from the lacrimal apparatus in the orbit to the paranasal sinus through an internal passage of the implant device, the method comprising:

with the implant device secured to an exterior of a carrier member of an implantation tool with a distal end of the implant device disposed toward a distal end of the implantation tool and a proximal end of the implant device disposed toward a proximal end of the implantation tool and with an implantation approach from the lacrimal apparatus in the orbit, advancing the implant device through the surgical path between the lacrimal apparatus in an orbit and the paranasal sinus until the implant device is in an implantation position with the distal end of the implant device disposed in the paranasal sinus and the proximal end of the implant device disposed in the lacrimal apparatus in the orbit;

after the advancing, releasing the implant device from securement to the exterior of the carrier member and withdrawing the carrier member from the surgical path to leave the implant device implanted in the implantation position fluidly connecting the lacrimal apparatus in the orbit with the paranasal sinus through the internal passage of the implant device; and the implant device having a length from the proximal end to the distal end of the implant device;

wherein during the advancing a length portion of the implant device, which is smaller than the length of the implant device, enters into and advances at least some distance through the surgical path, and a majority of the length portion is in tension while advancing through the surgical path.

89. The method according to example combination 88, wherein the implantation tool is according to any one of example combinations 1-69 and the releasing the implant device comprises manipulating the release mechanism to reconfigure the securement mechanism from the securement configuration to the released configuration.

90. The method according to either one of example combination 88 or example combination 89, wherein during the advancing, the implant device and the implantation tool are in an implantation assembly according to any one of example combinations 70-79.

91. The method, implantation assembly or kit according to any one of example combinations 79, 84 and 87-90, wherein the length portion is in a range of from 8 millimeters to 40 millimeters.

92. The method, implantation assembly or kit according to any one of example combinations 79, 84, and 87-91, wherein the length of the implant device is in a range of from 10 millimeters to 45 millimeters.

93. The method, implantation assembly or kit according to any one of example combinations 79, 84, 87 and 87-92, wherein the length of the implant device is up to 2 millimeters longer than the length portion.

94. The method, implantation assembly or kit according to any one of example combinations 79, 84, 87 and 87-93, wherein the length of the implant device is at least 0.15 millimeters larger than the length portion.

95. The method, implantation assembly or kit according to any one of example combinations 79, 84, 87 and 87-94, wherein the length of the implant device and the length portion are each at least 12 millimeters.

96. The method, implantation assembly or kit according to any one of example combinations 79, 84, 87 and 87-95, wherein the length of the implant device and the length portion are each at least 15 millimeters.

97. The method, implantation assembly or kit according to any one of example combinations 79, 84, 87 and 87-96, wherein the length of the implant device and the length portion are each no larger than 30 millimeters.

98. The method, implantation assembly or kit according to any one of example combinations 79, 84, 87 and 87-97, wherein the implant device is secured to the carrier member by securement members that extend over an exterior of the implant device only on a distal portion of the implant device within a length distance of less than 50% (one-half) of the length portion along the length of the implant device from the distal end of the implant device, and optionally less than 30%, less than 25%, less than 20% or less than 15% of the length portion along the length of the implant device from the distal end of the implant device, and further optionally at least 5% of the length portion along the length of the implant device from the distal end of the implant device.

99. The method, implantation assembly or kit according to example combination 98, wherein the length distance is not larger than one-third of the length portion from the distal end of the implant device.

100. The method, implantation assembly or kit according to either one of example combination 98 or example combination 99, wherein the length distance is not larger than 5 millimeters from the distal end of the implant device, and optionally is not larger than 4 millimeters, not larger than 3 millimeters or not larger than 2.5 millimeters from the distal end of the implant device, and further optionally is at least 0.5 millimeter or at least 1 millimeter from the distal end of the implant device.

101. The method, implantation assembly or kit according to any one of example combination 98-100, wherein the length distance is not greater than 3 millimeters from the distal end of the implant device.

102. The implantation tool, implantation assembly, kit or method according to any one of example combinations 1-101, wherein the implantation tool comprises the securement mechanism according to any of example combinations 2-35 and one or more said securement members is integral with the carrier member.

103. The implantation tool, implantation assembly, kit or method according to example combination 102, wherein the implantation tool comprises a sheath member as recited in any one of example combinations 32-34 and the sheath member is integral with the carrier member.

104. The implantation tool, implantation assembly, kit or method according to any one of example combinations 1-103, wherein the implantation tool comprises a securement member according to any one of example combinations 2-35 comprising a material of construction selected from the group consisting of a polyimides, a polyamides (e.g., a nylon), a Mylar, a PET (polyethylene terephthalate), a FEP (fluorinated ethylene propylene), a PTFE (polytetrafluoroethylene), a nitinol suture material, a PVF (polyvinyl fluorides), a composite polymer and a silicone composite composition.

105. The implantation tool, implantation assembly, kit or method according to any one of example combinations 1-103, wherein the implantation tool comprises a securement member according to any one of example combinations 2-35 comprising a polyether block amide elastomer as a material of construction.

The foregoing description of the present invention and various aspects thereof has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

The description of a feature or features in a particular combination do not exclude the inclusion of an additional feature or features in a variation of the particular combination. Processing steps and sequencing are for illustration only, and such illustrations do not exclude inclusion of other steps or other sequencing of steps to an extent not necessarily incompatible. Additional steps may be included between any illustrated processing steps or before or after any illustrated processing step to an extent not necessarily incompatible.

The terms "comprising", "containing", "including" and "having", and grammatical variations of those terms, are intended to be inclusive and nonlimiting in that the use of such terms indicates the presence of a stated condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or any appropriate grammatical variation of such narrower terms). For example, a statement that something "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

What is claimed is:

1. An implantation tool configured to implant a paranasal sinus fluid access implant device with an internal fluid communication passage through an artificial, surgical path between a lacrimal apparatus in the orbit and a paranasal sinus in an implantation procedure to provide direct fluid communication access through the internal passage from the lacrimal apparatus in the orbit to the paranasal sinus, the implantation tool comprising:

a carrier member configured to carry the implant device on a mounting portion of the carrier member in an implantation orientation to position the implant device in an implantation position through the surgical path from an approach through the palpebral fissure during the implantation procedure;

a securement mechanism configured to secure the implant device in an implantation orientation on the carrier member to carry the implant device to the implantation position during the implantation procedure, the securement mechanism being reconfigurable from a securement configuration to secure the implant device to the mounting portion of the carrier member in the implantation orientation to a released configuration to release the implant device from securement to the carrier member to permit withdrawal of the carrier member relative to the implant device to leave the implant device implanted in the implantation position during the implantation procedure, wherein the securement mechanism comprises at least one securement member positioned to extend over and press against an exterior portion of the implant device in the implantation orientation when the securement mechanism is in the securement configuration;

a handle portion connected with the carrier member and configured to remain outside of the surgical path during the implantation procedure and being manipulable by a medical practitioner to direct implantation of the implant device during the implantation procedure;

an internal working space housed within at least a portion of the handle portion and at least a portion of the carrier member;

a release mechanism disposed at least in part in the internal working space and manipulable to reconfigure the securement mechanism from the securement configuration to the released configuration; and a slidable member disposed at least in part in the internal working space in the carrier member, and the securement mechanism comprises a retainment structure on the slidable member to engage and retain a distal portion of at least one said securement member in the securement configuration.

2. The implantation tool according to claim 1, wherein the securement mechanism comprises at least two said securement members each positioned to extend over and press against said exterior portion of the implant device when the securement mechanism is in the securement configuration.

3. The implantation tool according to claim 1, wherein at least one of said securement member extends distal to a distal end of the mounting portion of the carrier member in the securement configuration to cover a distal end portion of the implant device when mounted on the mounting portion in the implantation orientation.

4. The implantation tool according to claim 3, comprising at least two said securement members each extending distal to a distal end of the mounting portion of the carrier member in the securement configuration, to cover a distal end portion of the implant device when mounted on the mounting portion in the implantation orientation.

5. The implantation tool according to claim 1, wherein each said securement member is in tension in the securement configuration.

6. The implantation tool according to claim 1, comprising at least two said securement members, and wherein:
the slidable member comprises at least two said retainment structures, each to engage and retain a distal portion of a different securement member in the securement configuration.

7. The implantation tool according to claim 6, wherein the slidable member is in a first position when the securement mechanism is in the securement configuration and is in a second position when the securement mechanism is in the released configuration.

8. The implantation tool according to claim 7, wherein the second position is slidably retracted toward a proximal end of the implantation tool relative to the first position.

9. The implantation tool according to claim 8, wherein the release mechanism comprises a translation path within the internal working space in which at least a proximal portion of the slidable member is slidable when slidably repositioning the slidable member from the first position to the second position.

10. The implantation tool according to claim 9, wherein the release mechanism comprises a spring mechanism in a charged state applying a biasing force to the slidable member when the slidable member is in at least one of the first position and the second position.

11. The implantation tool according to claim 10, wherein the spring mechanism is in the charged state when the slidable member is in the first position with the biasing force directed to urging the slidable member toward the second position.

12. The implantation tool according to claim 11, wherein the release mechanism comprises an actuator mechanism retained in a locked configuration maintaining the spring mechanism in the charged state with the slidable member in the first position, and wherein:
the actuator mechanism is hand manipulable to release the actuator mechanism from the locked configuration to release the spring mechanism from the charged state to propel the slidable member to the second position.

13. The implantation tool according to claim 12, wherein the charged state is a compressed state, and the release of the actuator mechanism from the locked configuration permits expansion of the spring from the compressed state.

14. The implantation tool according to claim 12, wherein the actuator mechanism comprises a movable actuation member that is hand movable to release the actuator mechanism from the locked configuration, and
the implantation tool comprises a safety cover selectively movable to selectively cover and uncover the movable actuation member to permit and prevent hand access to the movable actuation member.

15. The implantation tool according to claim 14, wherein the movable actuator member is a depressable member.

16. The implantation tool according to claim 1, wherein the slidable member has a lumen therethrough configured for passage therethrough of a guide wire to guide a distal end of the implantation tool to the surgical path during an implantation procedure.

17. The implantation tool according to claim 1, wherein said retainment structure and said distal portion of said securement member engaged with said retainment structure in the securement configuration are disposed distal of a distal end of the internal working space in the carrier member.

18. The implantation tool according to claim 17, wherein each said retainment structure and each said distal portion of a securement member engaged with said retainment structure in the securement configuration are disposed distal of a distal end of the internal working space in the carrier member.

19. The implantation tool according to claim 1, wherein at least one said securement member is configured to extend from inside the interior passage of said implant device mounted in the implantation orientation on the implant portion of the carrier member, through a side port of the implant device to outside of the implant device, from the side port over said exterior portion of the implant device to a distal end of the implant device and distal to the distal end of the implant device.

20. The implantation tool according to claim 19, wherein at least two said securement members are each configured to extend from inside the interior passage of said implant device mounted in the implantation orientation on the implant portion of the carrier member, through a different said side port of the implant device to outside of the implant device, from the side port over said exterior portion of the implant device to said distal end of the implant device and distal to the distal end of the implant device.

21. The implantation tool according to claim 20, wherein each said securement member configured to extend through said side port has a maximum cross-dimension in a range of from 0.55 millimeter to 0.85 millimeter.

22. The implantation tool according to claim 1, wherein said securement member comprises a snare member retained in a snare loop to press against an exterior portion of a portion of said implant device received through the snare loop when the securement mechanism is in the securement configuration.

23. The implantation tool according to claim 22, wherein the snare member is released from the snare loop when the securement mechanism is in the released configuration.

24. The implantation tool according to claim 1, wherein the length of the mounting portion of the carrier member is in a range of from 8 millimeters to 45 millimeters.

25. The implantation tool according to claim 24, wherein the carrier member has a cross-section at a proximal end of the mounting portion with a maximum cross-dimension of the cross section in a range of from 0.7 to 1.2 millimeters.

26. The implantation tool according to claim 25, wherein the implantation tool has a length in a range of from 100 millimeters to 150 millimeters.

27. An implantation assembly for implanting a paranasal sinus fluid access implant device through a surgical path between a lacrimal apparatus in the orbit and a paranasal sinus in an implantation procedure to provide direct fluid communication access from the lacrimal apparatus in the orbit to the paranasal sinus through an internal passage of the implant device, the implantation assembly comprising:
the implant device: and
the implantation tool according to claim 1, wherein the implant device is mounted in the mounting orientation on the mounting portion of the carrier member with the securement mechanism in the securement configuration.

28. The implantation assembly according to claim 27, wherein the carrier member secures the implant device by passing outside the internal passage of the implant device.

29. The implantation assembly according to claim 28, wherein the internal passage of the implant device is collapsed at a location of securement to the mounting portion of the carrier member by the securement mechanism.

30. The implantation assembly according to claim 27, wherein the securement mechanism secures the implant device to the carrier member at securement locations, and wherein none of the securement locations are disposed more than 5 millimeters proximal of a distal end of the implant device along the length of the carrier member.

31. The implantation assembly according to claim 30, wherein the securement mechanism does not contact said exterior of the implant device at any location on the implant device disposed more than 5 millimeters from a distal end of the implant device.

32. The implantation assembly according to claim 30, wherein:
the implant device comprises an exterior anchor surface feature to anchor the implant device in tissue between the lacrimal apparatus in the orbit and the paranasal sinus, wherein the exterior anchor surface feature comprises anchor protrusions and recess areas defined between adjacent anchor protrusions, wherein the anchor protrusions and recesses are configured to engage the tissue; and
the securement mechanism contacts said exterior of the implant device extending over at least one anchor protrusion.

33. An implantation tool configured to implant a paranasal sinus fluid access implant device with an internal fluid communication passage through an artificial, surgical path between a lacrimal apparatus in the orbit and a paranasal sinus in an implantation procedure to provide direct fluid communication access through the internal passage from the lacrimal apparatus in the orbit to the paranasal sinus, the implantation tool comprising:
a carrier member configured to carry the implant device on a mounting portion of the carrier member in an implantation orientation to position the implant device in an implantation position through the surgical path from an approach through the palpebral fissure during the implantation procedure;
a securement mechanism configured to secure the implant device in the implantation orientation on the carrier member to carry the implant device to the implantation position during the implantation procedure, the securement mechanism being reconfigurable from a securement configuration to secure the implant device to the mounting portion of the carrier member in the implantation orientation to a released configuration to release the implant device from securement to the carrier member to permit withdrawal of the carrier member relative to the implant device to leave the implant device implanted in the implantation position during the implantation procedure;
a handle portion connected with the carrier member and configured to remain outside of the surgical path during the implantation procedure and being manipulable by a medical practitioner to direct implantation of the implant device during the implantation procedure;
an internal working space housed within at least a portion of the handle portion and at least a portion of the carrier member;
a release mechanism disposed at least in part in the internal working space and manipulable to reconfigure the securement mechanism from the securement configuration to the released configuration, wherein at least one said securement member comprises a sheath member configured to extend over a distal end of the implant device in the implantation orientation when the securement mechanism is in the securement configuration; and
the sheath member is configured to cover a radial portion of a circumference around the distal end of the implant device in the implantation orientation when the securement mechanism is in the securement configuration.

* * * * *